(12) United States Patent
Cao et al.

(10) Patent No.: US 11,815,636 B2
(45) Date of Patent: *Nov. 14, 2023

(54) RADIATION DETECTOR CAPABLE OF NOISE HANDLING

(71) Applicant: SHENZHEN XPECTVISION TECHNOLOGY CO., LTD., Shenzhen (CN)

(72) Inventors: Peiyan Cao, Shenzhen (CN); Yurun Liu, Shenzhen (CN)

(73) Assignee: SHENZHEN XPECTVISION TECHNOLOGY CO., LTD., Shenzhen (CN)

(*) Notice: Subject to any disclaimer, the term of this patent is extended or adjusted under 35 U.S.C. 154(b) by 0 days.

This patent is subject to a terminal disclaimer.

(21) Appl. No.: 17/981,755

(22) Filed: Nov. 7, 2022

(65) Prior Publication Data

US 2023/0065682 A1 Mar. 2, 2023

Related U.S. Application Data

(63) Continuation of application No. 16/852,822, filed on Apr. 20, 2020, now Pat. No. 11,520,065, which is a
(Continued)

(51) Int. Cl.
*G01T 1/24* (2006.01)
*A61B 6/03* (2006.01)
*G01T 1/16* (2006.01)

(52) U.S. Cl.
CPC .......... *G01T 1/248* (2013.01); *A61B 6/032* (2013.01); *G01T 1/1603* (2013.01)

(58) Field of Classification Search
None
See application file for complete search history.

(56) References Cited

U.S. PATENT DOCUMENTS 11,520,065 B2 * 12/2022 Cao .................. A61B 6/032
2005/0032488 A1 2/2005 Pehlke et al.
(Continued)

FOREIGN PATENT DOCUMENTS

CN 101246047 A 8/2008
CN 103152531 A 6/2013
(Continued)

OTHER PUBLICATIONS

Long Dong, et al. Design of the X-ray Single Photon Detection Circuit Based on Si-APD. Spacecraft Recovery and Remote Sensing 37.1 (2016): 55-62. DOI: 10.3969/j.issn.1009-8518.2016.01.007.

*Primary Examiner* — Hoon K Song
(74) *Attorney, Agent, or Firm* — IPRO, PLLC; Qian Gu

(57) ABSTRACT

Disclosed herein is a radiation detector, comprising: an avalanche photodiode (APD) with a first side coupled to an electrode and configured to work in a linear mode; a capacitor module electrically connected to the electrode and comprising a capacitor, wherein the capacitor module is configured to collect charge carriers from the electrode onto the capacitor; a current sourcing module in parallel to the capacitor, the current sourcing module configured to compensate for a leakage current in the APD and comprising a current source and a modulator; wherein the current source is configured to output a first electrical current and a second electrical current; wherein the modulator is configured to control a ratio of a duration at which the current source outputs the first electrical current to a duration at which the current source outputs the second electrical current.

23 Claims, 29 Drawing Sheets

Related U.S. Application Data continuation of application No. PCT/CN2017/107775, filed on Oct. 26, 2017.

(56) References Cited

U.S. PATENT DOCUMENTS

| | | |
|---|---|---|
| 2005/0248376 A1 | 11/2005 | Boerstler et al. |
| 2006/0056581 A1 | 3/2006 | Hoffman et al. |
| 2012/0194264 A1 | 8/2012 | Chamakura |
| 2017/0031009 A1 | 2/2017 | Davidovic et al. |
| 2017/0160129 A1 | 6/2017 | Viswanath et al. |

FOREIGN PATENT DOCUMENTS

| | | |
|---|---|---|
| JP | 2004264097 A | 9/2004 |
| WO | 2016161542 A1 | 10/2016 |

\* cited by examiner

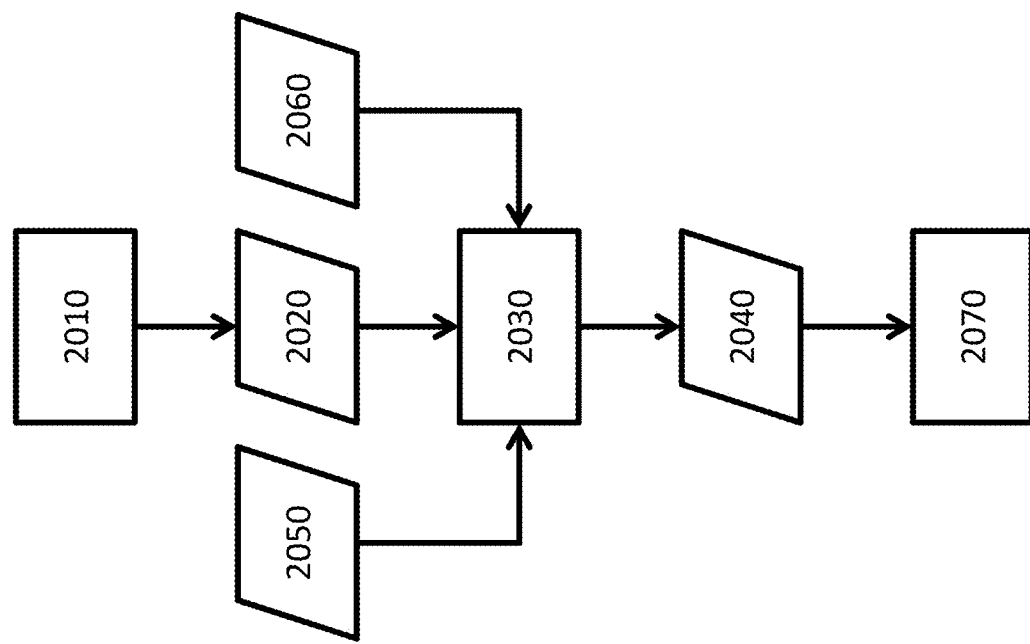

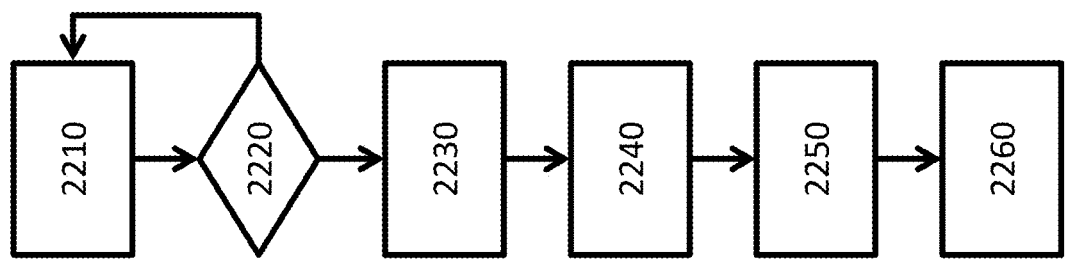

RADIATION DETECTOR CAPABLE OF NOISE HANDLING

TECHNICAL FIELD

The disclosure herein relates to radiation detectors, particularly relates to radiation detectors based on avalanche diodes capable of noise handling.

BACKGROUND

A radiation detector is a device that measures a property of a radiation. Examples of the property may include a spatial distribution of the intensity, phase, and polarization of the radiation. The radiation may be one that has interacted with a subject. For example, the radiation measured by the radiation detector may be a radiation that has penetrated or reflected from the subject. The radiation may be an electromagnetic radiation such as infrared light, visible light, ultraviolet light, X-ray or γ-ray. The radiation may be of other types such as α-rays and β-rays.

One type of radiation detectors is based on interaction between the radiation and a semiconductor. For example, a radiation detector of this type may have a semiconductor layer that absorbs the radiation and generate charge carriers (e.g., electrons and holes) and circuitry for detecting the charge carriers.

Radiation detectors may be negatively impacted by "dark" noise (e.g., leakage current). Dark noise in a radiation detector includes physical effects present even if no radiation the radiation detector is configured to detect is incident on the radiation detector. Isolating or reducing the impact of the dark noise to the overall signals detected by the radiation detector is helpful to make the radiation detector more useful.

SUMMARY

Disclosed herein is a radiation detector, comprising: an avalanche photodiode (APD) with a first side coupled to an electrode and configured to work in a linear mode; a capacitor module electrically connected to the electrode and comprising a capacitor, wherein the capacitor module is configured to collect charge carriers from the electrode onto the capacitor; a current sourcing module in parallel to the capacitor, the current sourcing module configured to compensate for a leakage current of in the APD and comprising a current source and a modulator; wherein the current source is configured to output a first electrical current and a second electrical current; wherein the modulator is configured to control a ratio of a duration at which the current source outputs the first electrical current to a duration at which the current source outputs the second electrical current.

According to an embodiment, the current sourcing module is adjustable.

According to an embodiment, the current sourcing module is configured to divert the leakage current of the APD through the current sourcing module.

According to an embodiment, the first electrical current and the second electrical current are different in their magnitude, direction, or both.

According to an embodiment, least one of the first electrical current and the second electrical current is at least an order of magnitude larger than the leakage current of the APD.

According to an embodiment, the electrical current of the dark noise is from 1 pA to 1000 pA.

According to an embodiment, the modulator comprises a processor or a memory.

According to an embodiment, the modulator comprises a switch.

According to an embodiment, the radiation comprises soft X-ray, ultraviolet (UV) light or extreme ultraviolet (EUV) light.

According to an embodiment, the current source comprises a current mirror.

According to an embodiment, the modulator is located on an input stage of the current mirror.

According to an embodiment, the modulator comprises a current source configured to output electrical current at alternating magnitudes.

According to an embodiment, the modulator comprises a current source configured to output two magnitudes of electrical current with adjustable ratio of durations.

According to an embodiment, the modulator is located on an output stage of the current mirror.

According to an embodiment, the modulator comprises a switch configured to controllably connect the current sourcing module to and to controllably disconnect it from the capacitor.

According to an embodiment, the radiation detector further comprises: a first voltage comparator configured to compare a voltage of the electrode to a first threshold; a second voltage comparator configured to compare the voltage to a second threshold; a counter configured to register a number of photons absorbed by the absorption layer; a controller; wherein the controller is configured to start a time delay from a time at which the first voltage comparator determines that an absolute value of the voltage equals or exceeds an absolute value of the first threshold; wherein the controller is configured to activate the second voltage comparator during (including the beginning and the expiration) the time delay; wherein the controller is configured to cause the number registered by the counter to increase by one, if the second voltage comparator determines that an absolute value of the voltage equals or exceeds an absolute value of the second threshold.

According to an embodiment, the controller is configured to activate the second voltage comparator at a beginning or expiration of the time delay.

According to an embodiment, the apparatus further comprises a voltmeter and the controller is configured to cause the voltmeter to measure the voltage upon expiration of the time delay.

According to an embodiment, the controller is configured to determine an X-ray photon energy based on a value of the voltage measured upon expiration of the time delay.

According to an embodiment, the controller is configured to connect the electrode to an electrical ground.

According to an embodiment, a rate of change of the voltage is substantially zero at expiration of the time delay.

According to an embodiment, a rate of change of the voltage is substantially non-zero at expiration of the time delay.

According to an embodiment, the apparatus comprises an array of APDs.

Disclosed herein is a system comprising the apparatus described above and an X-ray source, wherein the system is configured to perform X-ray radiography on human chest or abdomen.

According to an embodiment, the system comprises the apparatus described above and an X-ray source, wherein the system is configured to perform X-ray radiography on human mouth.

Disclosed herein is a cargo scanning or non-intrusive inspection (NII) system, comprising the apparatus described above and an X-ray source, wherein the cargo scanning or non-intrusive inspection (NII) system is configured to form an image using backscattered X-ray.

Disclosed herein is a cargo scanning or non-intrusive inspection (NII) system, comprising the apparatus described above and an X-ray source, wherein the cargo scanning or non-intrusive inspection (NII) system is configured to form an image using X-ray transmitted through an object inspected.

Disclosed herein is a full-body scanner system comprising the apparatus described above and an X-ray source.

Disclosed herein is an X-ray computed tomography (X-ray CT) system comprising the apparatus described above and an X-ray source.

Disclosed herein is an electron microscope comprising the apparatus described above, an electron source and an electronic optical system.

Disclosed herein is a system comprising the apparatus described above, wherein the system is an X-ray telescope, or an X-ray microscopy, or wherein the system is configured to perform mammography, industrial defect detection, microradiography, casting inspection, weld inspection, or digital subtraction angiography.

Disclosed herein is a method comprising: determining a contribution of a leakage current in signals of an avalanche photodiode (APD) working in a linear mode; determining a ratio of a duration of a first compensatory signal to a duration of a second compensatory signal based on the contribution of the leakage current, the first compensatory signal and the second compensatory signal; and compensating the signals of the APD for the leakage current with the first compensatory signal and the second compensatory signal with their respective durations with the ratio.

According to an embodiment, the contribution is determined by measuring the signals while the APD receives no radiation.

According to an embodiment, the first compensatory signal and the second compensatory signal are electrical currents.

Disclosed herein is a method comprising: measuring signals of an avalanche photodiode (APD) working in a linear mode when the APD receives no radiation and a compensation for a leakage current of the APD is present; if the signals have exceeded a first level, commencing a time delay; measuring the signals of the APD at an end of the time delay; and if the signals at the end of the time delay exceed a second level, increasing the compensation for the leakage current.

According to an embodiment, the compensation is increased to a magnitude among a group of discrete values.

According to an embodiment, the method further comprises: if the signals at the end of the time delay exceed a second level, resetting the signals.

Disclosed herein is a method comprising: measuring signals of an avalanche photodiode (APD) working in a linear mode when the APD receives no radiation and a compensation for a leakage current of the APD is present; if the signals have exceeded a first level, commencing a time delay; measuring the signals of the APD at an end of the time delay; determining a difference between the signals at the end of the time delay and the signals at the beginning of the time delay; and determining a magnitude of the compensation based on the difference.

BRIEF DESCRIPTION OF FIGURES

FIG. 13 schematically shows a flow chart for a method of compensating for dark noise in a radiation detector.

FIG. 14B schematically shows a flow chart for a method of compensating for dark noise in a radiation detector.

DETAILED DESCRIPTION

An avalanche photodiode (APD) is a photodetector based on semiconductor material. For example, an APD may be in a form of a p-n junction under a reverse bias (i.e., the p-type region of the p-n junction is biased at a lower electric potential than the n-type region). The p-n junction may have a breakdown voltage. The breakdown voltage is a reverse bias, above which exponential increase in the electric current in the p-n junction may occur.

An APD may operate at one of two modes. In one mode, the reverse bias of the p-n junction may be above the breakdown voltage. Here the word "above" means that absolute value of the reverse bias is greater than the absolute value of the breakdown voltage. This mode may be referred to as Geiger-mode and an APD working in this mode may be referred to as a single-photon avalanche diode (SPAD) (also known as a Geiger-mode APD or G-APD). In another mode, the reverse bias of the p-n junction may be below the breakdown voltage and this mode may be referred to as linear mode.

When a photon (e.g., visible light, ultraviolet or extreme ultraviolet (EUV) light) incidents on an APD, it may generate charge carriers (electrons and holes). Some of the charge carriers may be accelerated by an electric field in the APD and may trigger a current by impact ionization (e.g., an avalanche current in the case of a SPAD). Impact ionization is a process in a material by which one energetic charge carrier can lose energy by the creation of other charge carriers. For example, in semiconductors, an electron (or hole) with enough kinetic energy can knock a bound electron out of its bound state (in the valence band) and promote it to a state in the conduction band, creating an electron-hole pair.

Figure 1A:
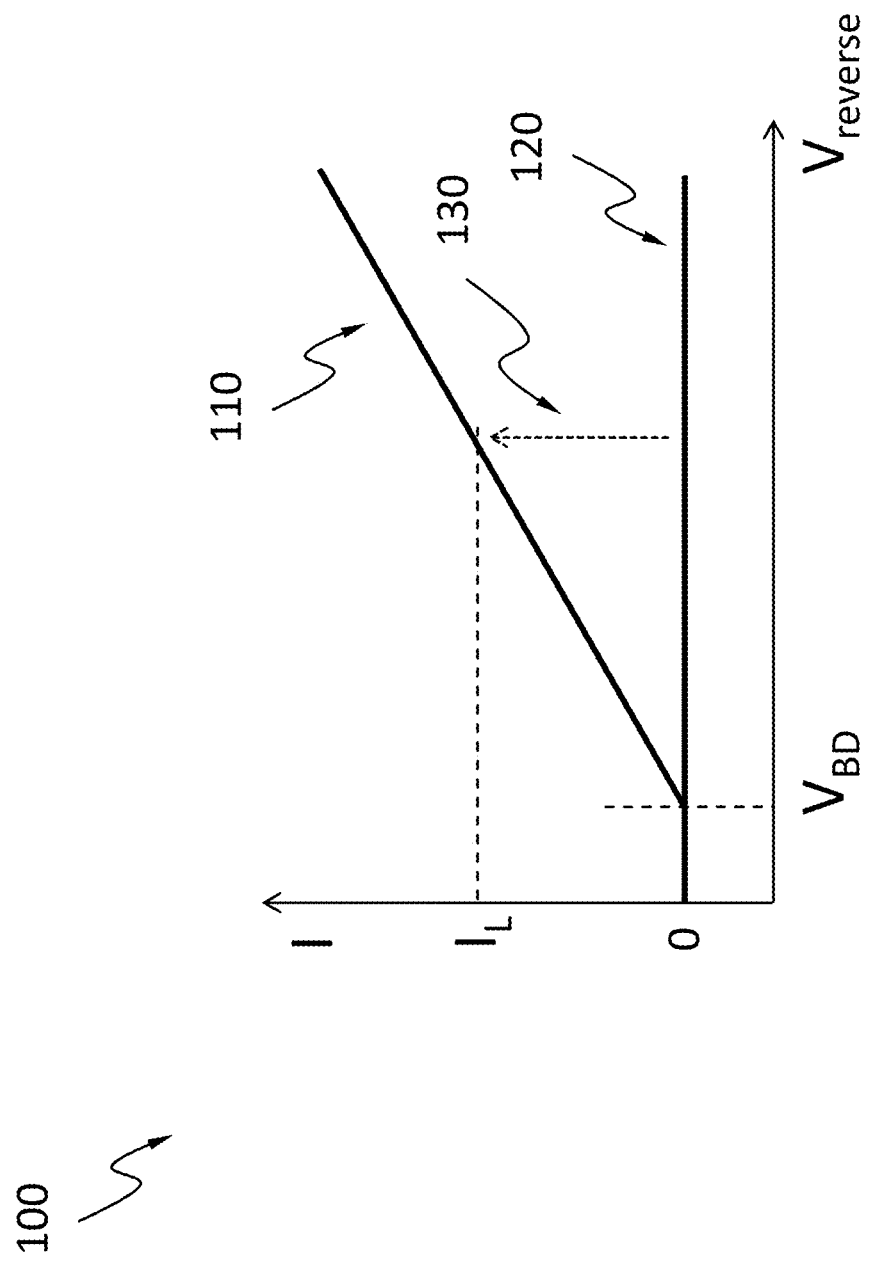
FIG. 1A schematically shows the current-voltage characteristics of an APD in the linear mode, and in the Geiger mode.

FIG. 1A schematically shows the current-voltage characteristics 100 of an APD in the linear mode, and in the Geiger mode (i.e., when the APD is a SPAD). The APD may have a bifurcation of the current-voltage characteristics 100 above the breakdown voltage $V_{BD}$ (i.e., a SPAD). When the reverse biased is above $V_{BD}$, both electrons and holes may cause significant ionization, and the avalanche is self-sustaining. When the avalanche is triggered (e.g., by an incident photon) at a reverse biased is above $V_{BD}$, the avalanche current is sustained ("on-branch" 110); when the avalanche is not triggered at a reverse biased is above $V_{BD}$, very little electric current flows through ("off-branch" 120). At a reverse bias above $V_{BD}$, when an incident photon triggers avalanche in the APD, the current-voltage characteristics 100 of the APD transitions (as indicated by the arrow 130) from the off-branch 120 to the on-branch 110. This transition manifests as a sharp increase of electric current flowing through the APD, from essentially zero to a finite value of $I_L$. This transition is similar to the mechanism behind the Geiger counter. Therefore, at a reverse bias above $V_{BD}$, an APD is operating in the "Geiger mode." An APD working at a reverse bias below the breakdown voltage is operating in the linear mode because the electric current in the APD is proportional to the intensity of the light incident on the APD.

Figure 1B:
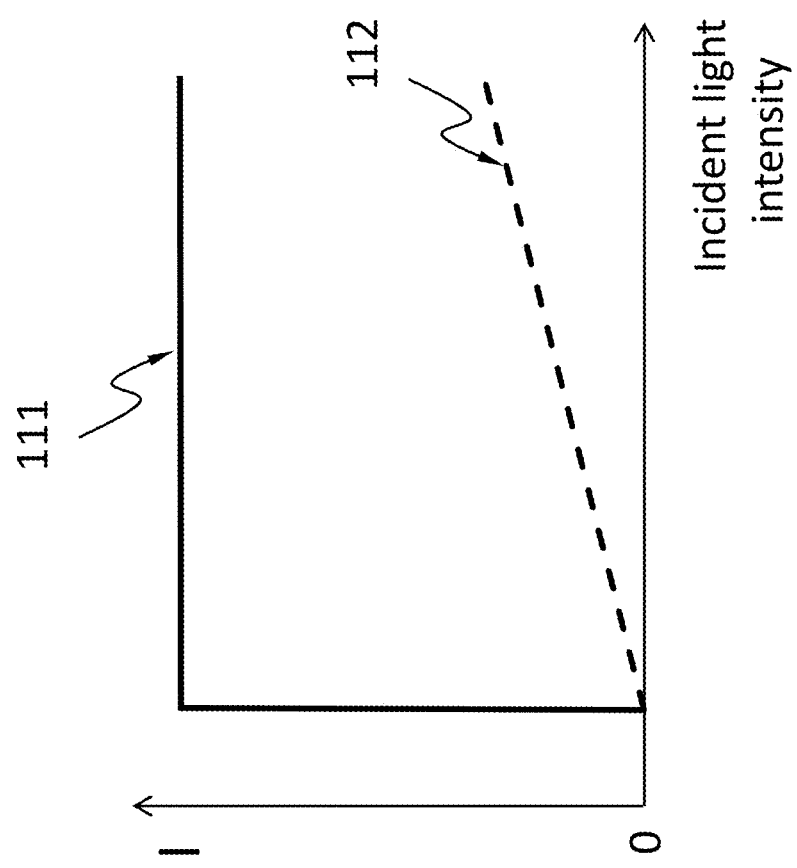
FIG. 1B schematically shows the electric current in an APD as a function of the intensity of light incident on the APD when the APD is in the linear mode, and a function of the intensity of light incident on the APD when the APD is in the Geiger mode.

FIG. 1B schematically shows the electric current in an APD as a function 112 of the intensity of light incident on the APD when the APD is in the linear mode, and a function 111 of the intensity of light incident on the APD when the APD is in the Geiger mode (i.e., when the APD is a SPAD). In the Geiger mode, the current shows a very sharp increase with the intensity of the light and then saturation. In the linear mode, the current is essentially proportional to the intensity of the light.

Figure 2C:
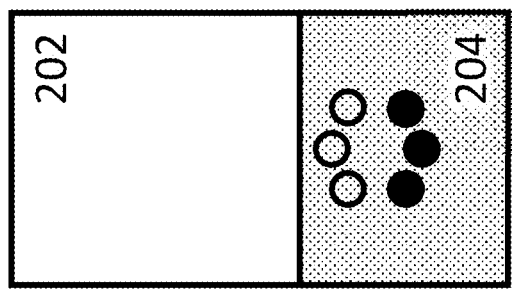
FIG. 2A, FIG. 2B and FIG. 2C schematically show the operation of an APD, according to an embodiment.
Figure 2B:
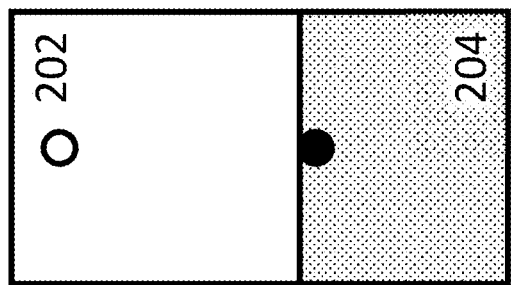
Figure 2A:
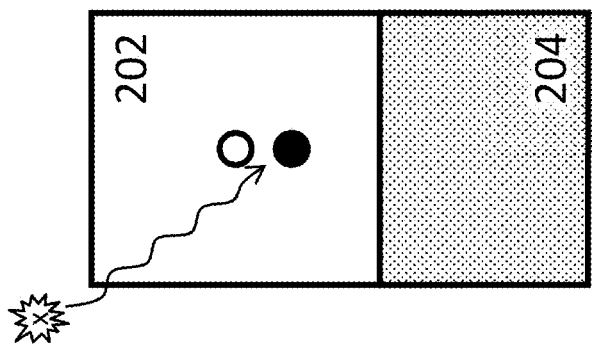

FIG. 2A, FIG. 2B and FIG. 2C schematically show the operation of an APD, according to an embodiment. FIG. 2A shows that when a photon (e.g., an X-ray photon) is absorbed by an absorption region 202, multiple (100 to 10000 for an X-ray photon) electron-hole pairs maybe generated. The absorption region 202 has a sufficient thickness and thus a sufficient absorptance (e.g., >80% or >90%) for the incident photon. For soft X-ray photons, the absorption region 202 may be a silicon layer with a thickness of 10 microns or above. The electric field in the absorption region 202 is not high enough to cause avalanche effect in the absorption region 202. FIG. 2B shows that the electrons and hole drift in opposite directions in the absorption region 202. FIG. 2C shows that avalanche effect occurs in an amplification region 204 when the electrons (or the holes) enter that amplification region 204, thereby generating more electrons and holes. The electric field in the amplification region 204 is high enough to cause an avalanche of charge carriers entering the amplification region 204 but not too high to make the avalanche effect self-sustaining. A self-sustaining avalanche is an avalanche that persists after the external triggers disappear, such as photons incident on the APD or charge carriers drifted into the APD. The electric field in the amplification region 204 may be a result of a doping profile in the amplification region 204. For example, the amplification region 204 may include a p-n junction or a heterojunction that has an electric field in its depletion zone. The threshold electric field for the avalanche effect (i.e., the electric field above which the avalanche effect occurs and below which the avalanche effect does not occur) is a property of the material of the amplification region 204. The amplification region 204 may be on one or two opposite sides of the absorption region 202.

Figure 3A:
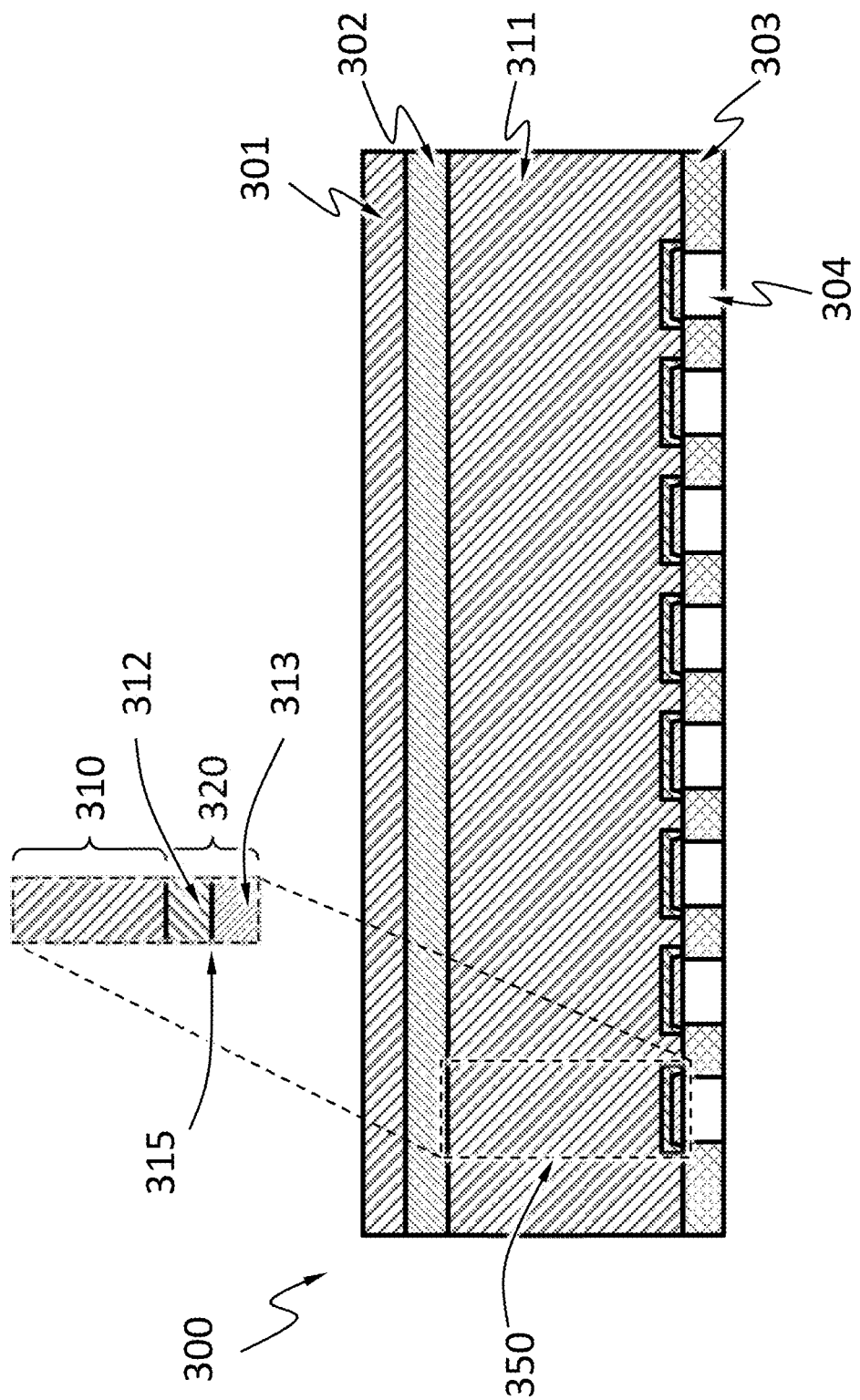
FIG. 3A schematically shows a cross section of a radiation detector based on an array of APDs.

FIG. 3A schematically shows a cross section of a radiation detector 300 based on an array of APDs 350. Each of the APDs 350 may have an absorption region 310 and an amplification region 320 as the example shown in FIG. 2A, FIG. 2B and FIG. 2C. At least some, or all, of the APDs 350 in the radiation detector 300 may have their absorption regions 310 joined together. Namely, the radiation detector 300 may have joined absorption regions 310 in a form of an absorption layer 311 that is shared among at least some or all of the APDs 350. The amplification regions 320 of the APDs 350 are discrete regions. Namely the amplification regions 320 of the APDs 350 are not joined together. In an embodiment, the absorption layer 311 may be in form of a semiconductor wafer such as a silicon wafer. The absorption regions 310 may be an intrinsic semiconductor or very lightly doped semiconductor (e.g., $<10^{12}$ dopants/cm$^3$, $<10^{11}$ dopants/cm$^3$, $<10^{10}$ dopants/cm$^3$, $<10^9$ dopants/cm$^3$), with a sufficient thickness and thus a sufficient absorptance (e.g., >80% or >90%) for incident photons of interest (e.g., X-ray photons). The amplification regions 320 may have a junction 315 formed by at least two layers 312 and 313. The junction 315 may be a heterojunction of a p-n junction. In an embodiment, the layer 312 is a p-type semiconductor (e.g., silicon) and the layer 313 is a heavily doped n-type layer (e.g., silicon). The phrase "heavily doped" is not a term of degree. A heavily doped semiconductor has its electrical conductivity comparable to metals and exhibits essentially linear positive thermal coefficient. In a heavily doped semiconductor, the dopant energy levels are merged into an energy band. A heavily doped semiconductor is also called degenerate semiconductor. The layer 312 may have a doping level of $10^{13}$ to $10^{17}$ dopants/cm$^3$. The layer 313 may have a doping level of $10^{18}$ dopants/cm$^3$ or above. The layers 312 and 313 may be formed by epitaxy growth, dopant implantation or dopant diffusion. The band structures and doping levels of the layers 312 and 313 can be selected such that the depletion zone electric field of the junction 315 is greater than the threshold electric field for the avalanche effect for electrons (or for holes) in the materials of the layers 312 and 313, but is not too high to cause self-sustaining avalanche. Namely, the depletion zone electric field of the junction 315 should cause avalanche when there are incident photons in the absorption region 310 but the avalanche should cease without further incident photons in the absorption region 310.

The radiation detector 300 may further include electrodes 304 respectively in electrical contact with the layer 313 of the APDs 350. The electrodes 304 are configured to collect electric current flowing through the APDs 350.

The radiation detector 300 may further include a passivation material 303 configured to passivate surfaces of the absorption regions 310 and the layer 313 of the APDs 350 to reduce recombination at these surfaces.

The radiation detector 300 may further include a heavily doped layer 302 disposed on the absorption regions 310 opposite to the amplification region 320, and a common electrode 301 on the heavily doped layer 302. The common electrode 301 of at least some or all of the APDs 350 may be joined together. The heavily doped layer 302 of at least some or all of the APDs 350 may be joined together.

When a photon (e.g., visible light, violet, ultraviolet or extreme ultraviolet (EUV)) incidents on the radiation detector 300, it may be absorbed by the absorption region 310 of one of the APDs 350, and charge carriers may be generated in the absorption region 310 as a result. One type (electrons or holes) of the charge carriers drift toward the amplification region 320 of that one APD. When the charge carriers enter the amplification region 320, the avalanche effect occurs and causes amplification of the charge carriers. The amplified charge carriers can be collected through the electrode 304 of that one APD, as an electric current. When that one APD is in the linear mode, the electric current is proportional to the number of incident photons in the absorption region 310 per unit time (i.e., proportional to the light intensity at that one APD). The electric currents at the APDs may be compiled to represent a spatial intensity distribution of light, i.e., an image. The amplified charge carriers may alternatively be collected through the electrode 304 of that one APD, and the number of photons may be determined from the charge carriers (e.g., by using the temporal characteristics of the electric current).

Figure 3B:
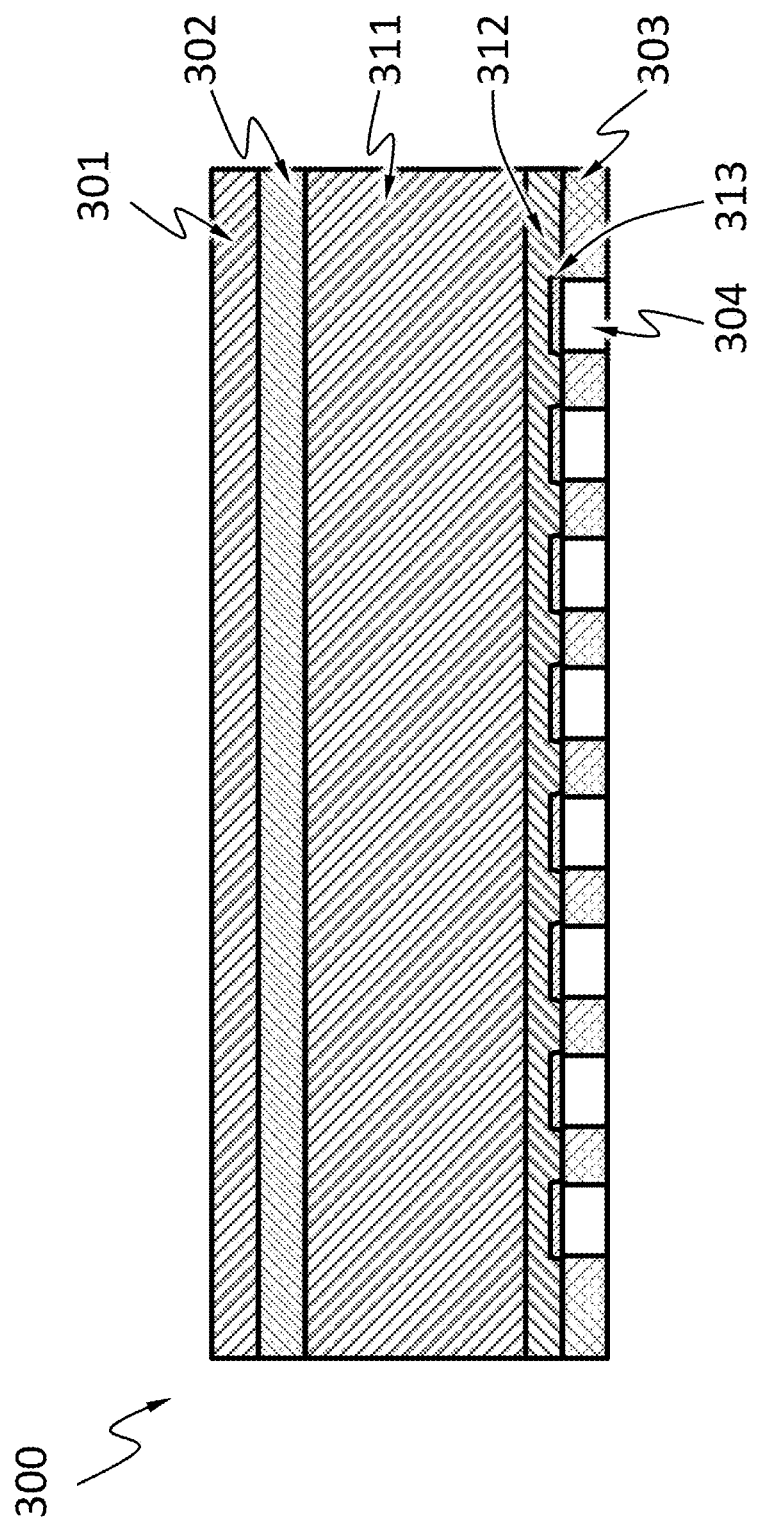
FIG. 3B shows a variant of the radiation detector of FIG. 3A.
Figure 3C:
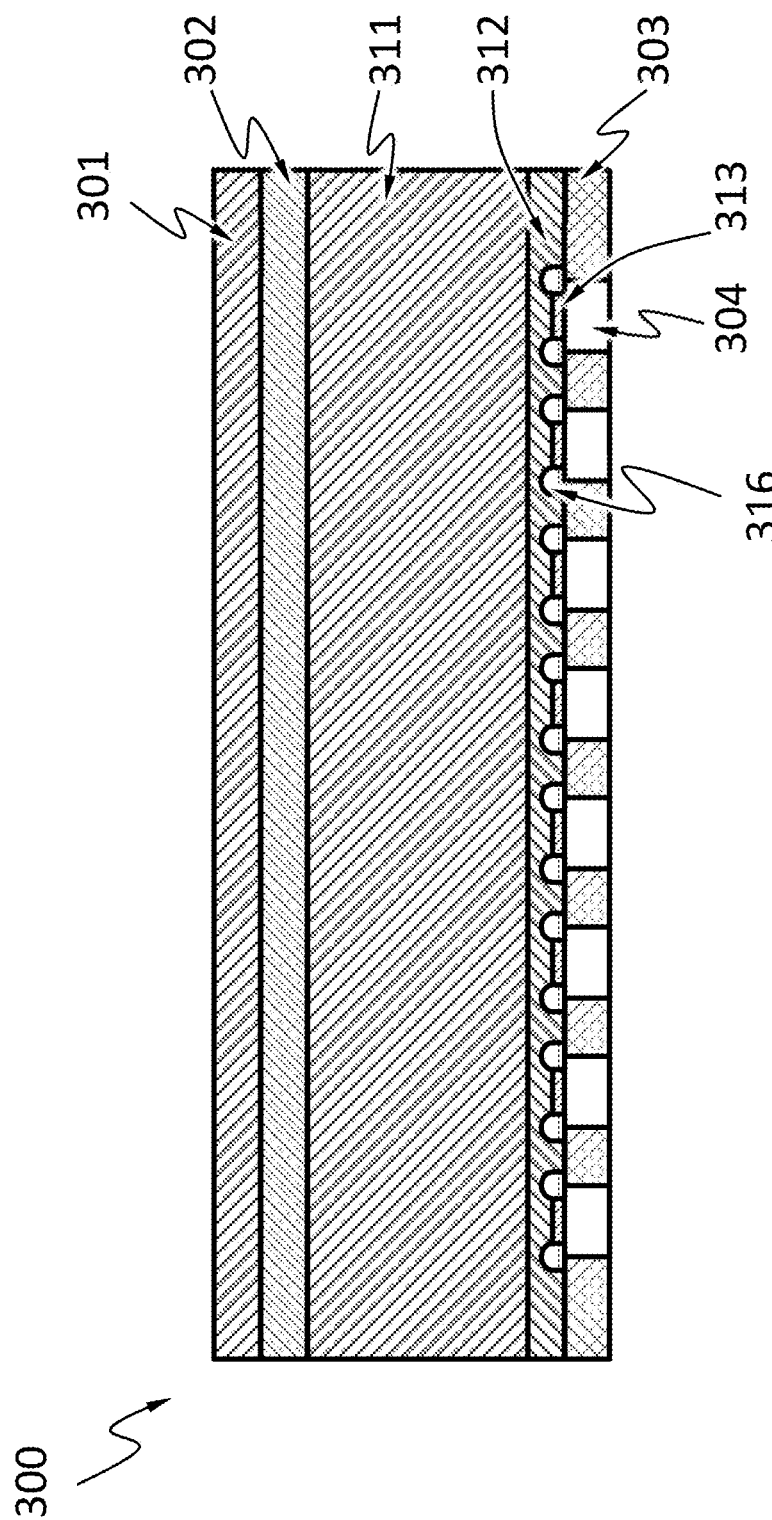
FIG. 3C shows a variant of the radiation detector of FIG. 3A.
Figure 3D:
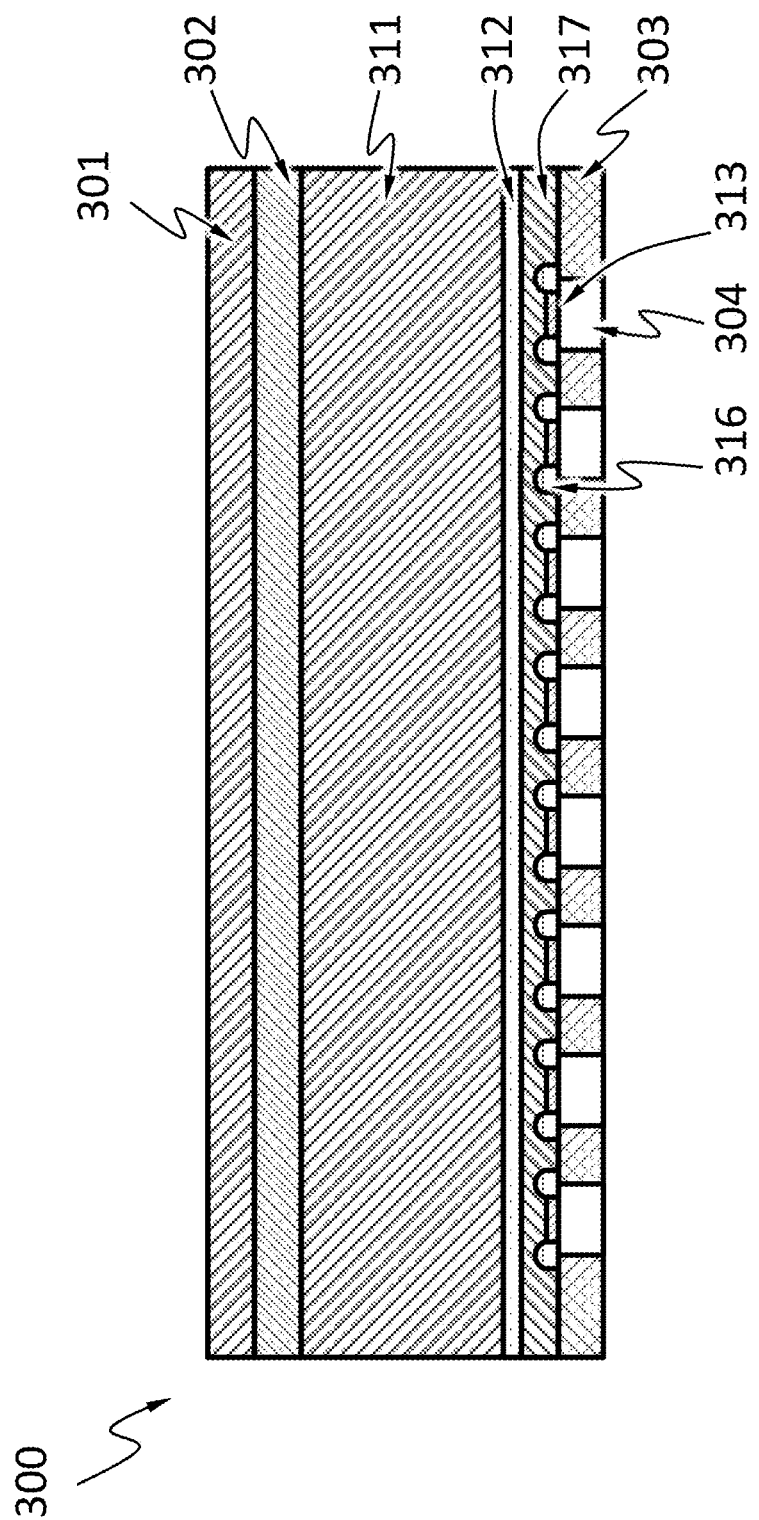
FIG. 3D shows a variant of the radiation detector of FIG. 3A.

The junctions 315 of the APDs 350 should be discrete, i.e., the junction 315 of one of the APDs should not be joined with the junction 315 of another one of the APDs. Charge carriers amplified at one of the junctions 315 of the APDs 350 should not be shared with another of the junctions 315. The junction 315 of one of the APDs may be separated from the junction 315 of the neighboring APDs by the material of the absorption region wrapping around the junction, by the material of the layer 312 or 313 wrapping around the junction, by an insulator material wrapping around the junction, or by a guard ring of a doped semiconductor. As shown in FIG. 3A, the layer 312 of each of the APDs 350 may be discrete, i.e., not joined with the layer 312 of another one of the APDs; the layer 313 of each of the APDs 350 may be discrete, i.e., not joined with the layer 313 of another one of the APDs. FIG. 3B shows a variant of the radiation detector 300, where the layers 312 of some or all of the APDs are joined together. FIG. 3C shows a variant of the radiation detector 300, where the junction 315 is surrounded by a guard ring 316. The guard ring 316 may be an insulator material or a doped semiconductor. For example, when the layer 313 is heavily doped n-type semiconductor, the guard ring 316 may be n-type semiconductor of the same material as the layer 313 but not heavily doped. The guard ring 316 may be present in the radiation detector 300 shown in FIG. 3A or FIG. 3B. FIG. 3D shows a variant of the radiation detector 300, where the junction 315 has an intrinsic semiconductor layer 317 sandwiched between the layer 312 and 313. The intrinsic semiconductor layer 317 in each of the APDs 350 may be discrete, i.e., not joined with other intrinsic semiconductor layer 317 of another APD. The intrinsic semiconductor layers 317 of some or all of the APDs 350 may be joined together.

Figure 4A:
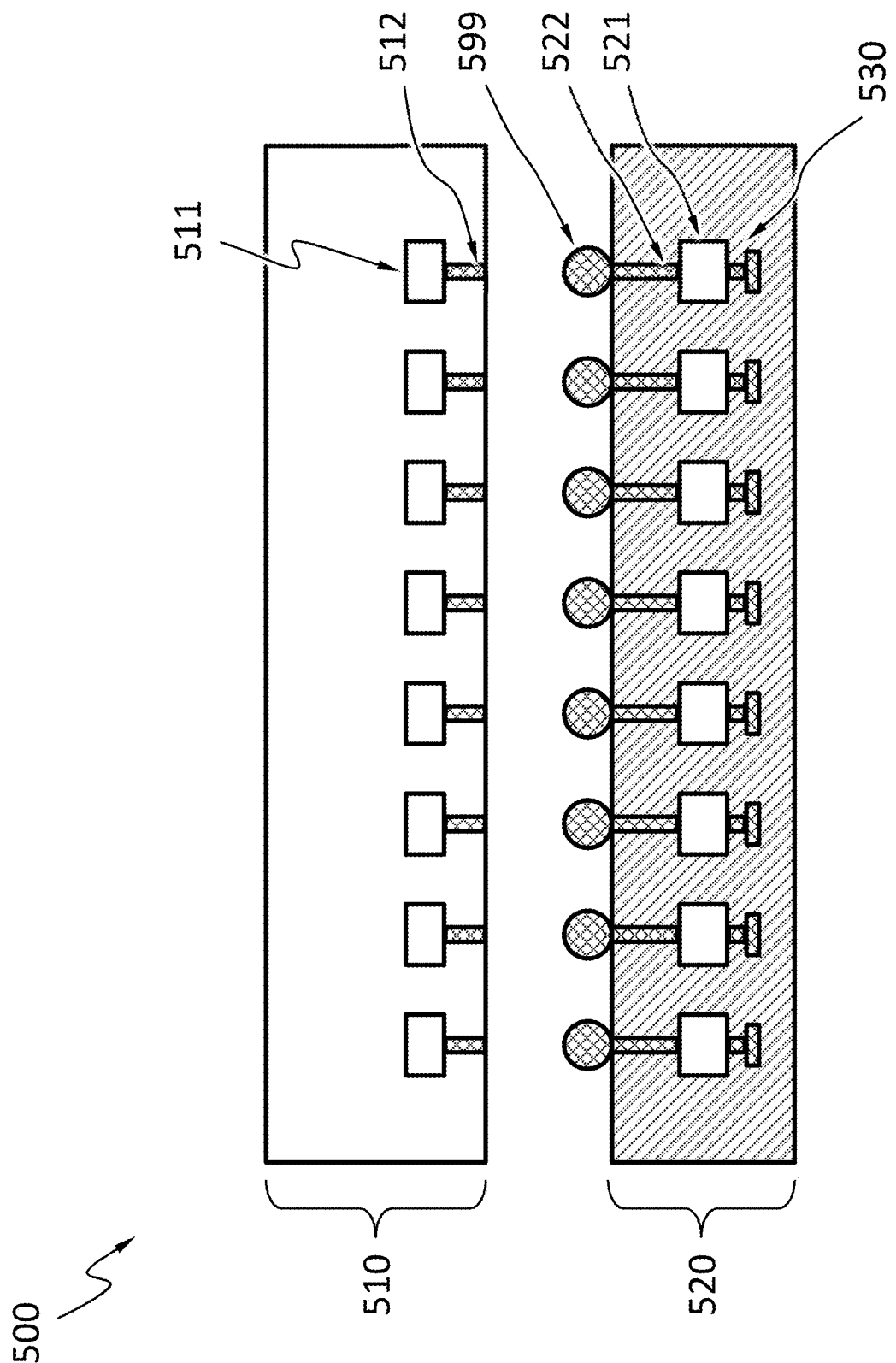
FIG. 4A and FIG. 4B schematically show a cross-sectional view of a radiation detector comprising a plurality of APDs.
Figure 4B:
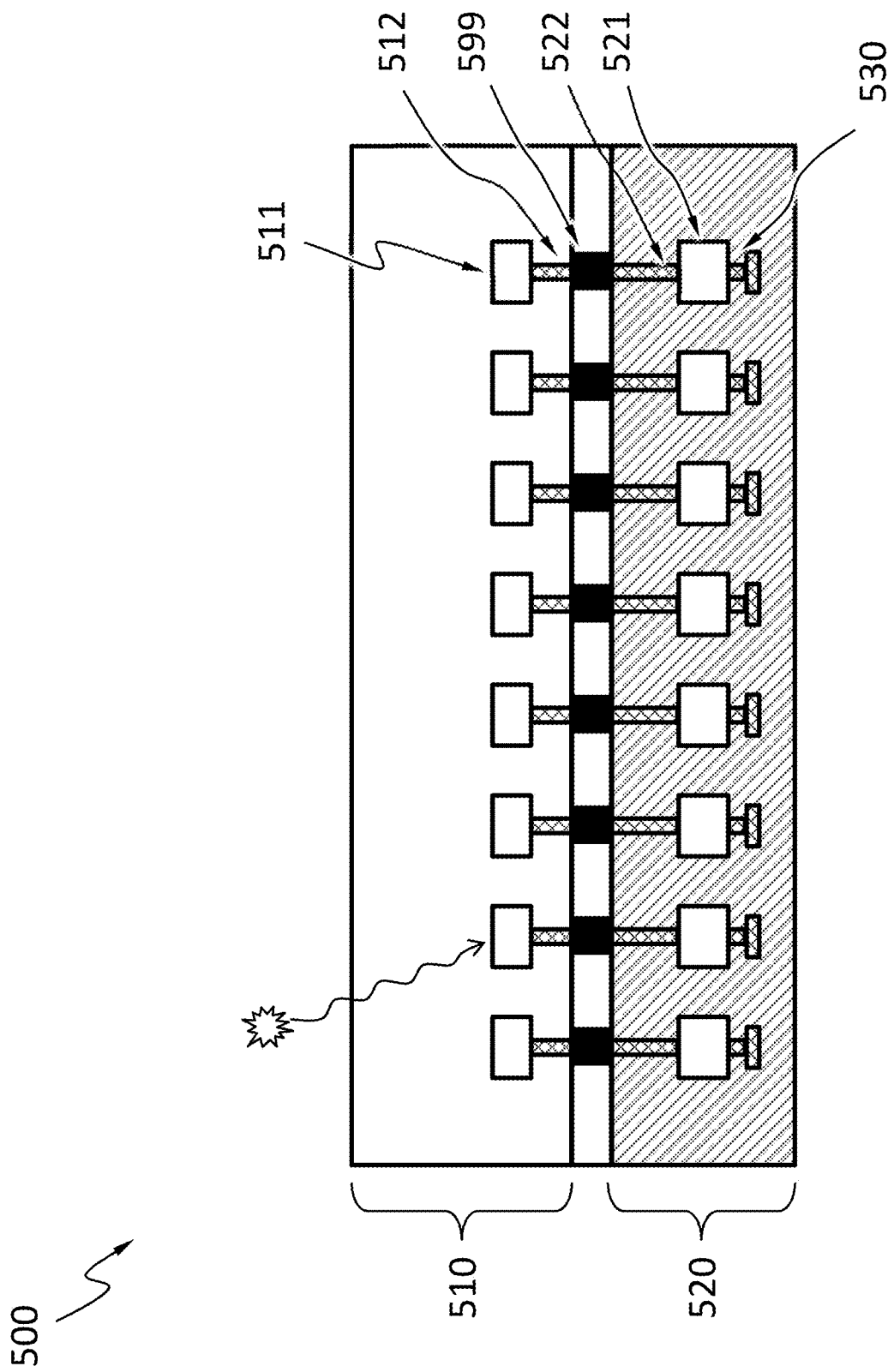

FIG. 4A and FIG. 4B schematically show a cross-sectional view of a radiation detector 500 comprising a plurality of APDs 511. The APDs 511 may be fabricated in a substrate 510 (e.g., a semiconductor wafer). One or more vias 512 may be present in the substrate 510 and the vias 512 electrically connect the APDs 511 to a surface of the substrate 510. Alternatively, the APDs 511 may be disposed on the surface of the substrate 510 such that electrical contacts on the APDs 511 are exposed to the surface. Electronic systems 521 that communicate and/or control the APDs 511 may be fabricated in another substrate 520. Electronic systems 521 may include controllers, bias sources, switches, current meters, memories, amplifiers or other suitable components. Some components of the electronic systems 521 may be fabricated in the substrate 510. Electronic systems 521 may be configured to use the APDs 511 using the method illustrated in FIG. 3. One or more vias 522 may be present and electrically connect the electronic systems 521 to a surface of the substrate 520. Alternatively, the electronic systems 521 may be disposed at the surface of the substrate 520 such that electrical contacts on the electronic systems 521 are exposed to the surface. The substrate 520 may include transmission lines 530 configured to transmit data, power and/or signals to and from the electronic systems 521, and through which to and from the APDs 511. The substrates 510 and 520 may be bonded by a suitable substrate bonding technique, such as flip chip bonding or direct bonding.

As shown in FIG. 4A and FIG. 4B, flip chip bonding uses solder bumps 599 deposited onto the surface of either one of the substrates 510 and 520. Either of the substrates 510 and 520 is flipped over and the APDs 511 and the electronic systems 521 are aligned (e.g., through the vias 512, 522 or both). The substrates 510 and 520 are brought into contact. The solder bumps 599 may be melted to electrically connect the APDs 511 and the electronic systems 521. Any void space among the solder bumps 599 may be filled with an insulating material.

Direct bonding is a wafer bonding process without any additional intermediate layers (e.g., solder bumps). The bonding process is based on chemical bonds between two surfaces. Direct bonding may be at elevated temperature but not necessarily so.

Figure 5A:
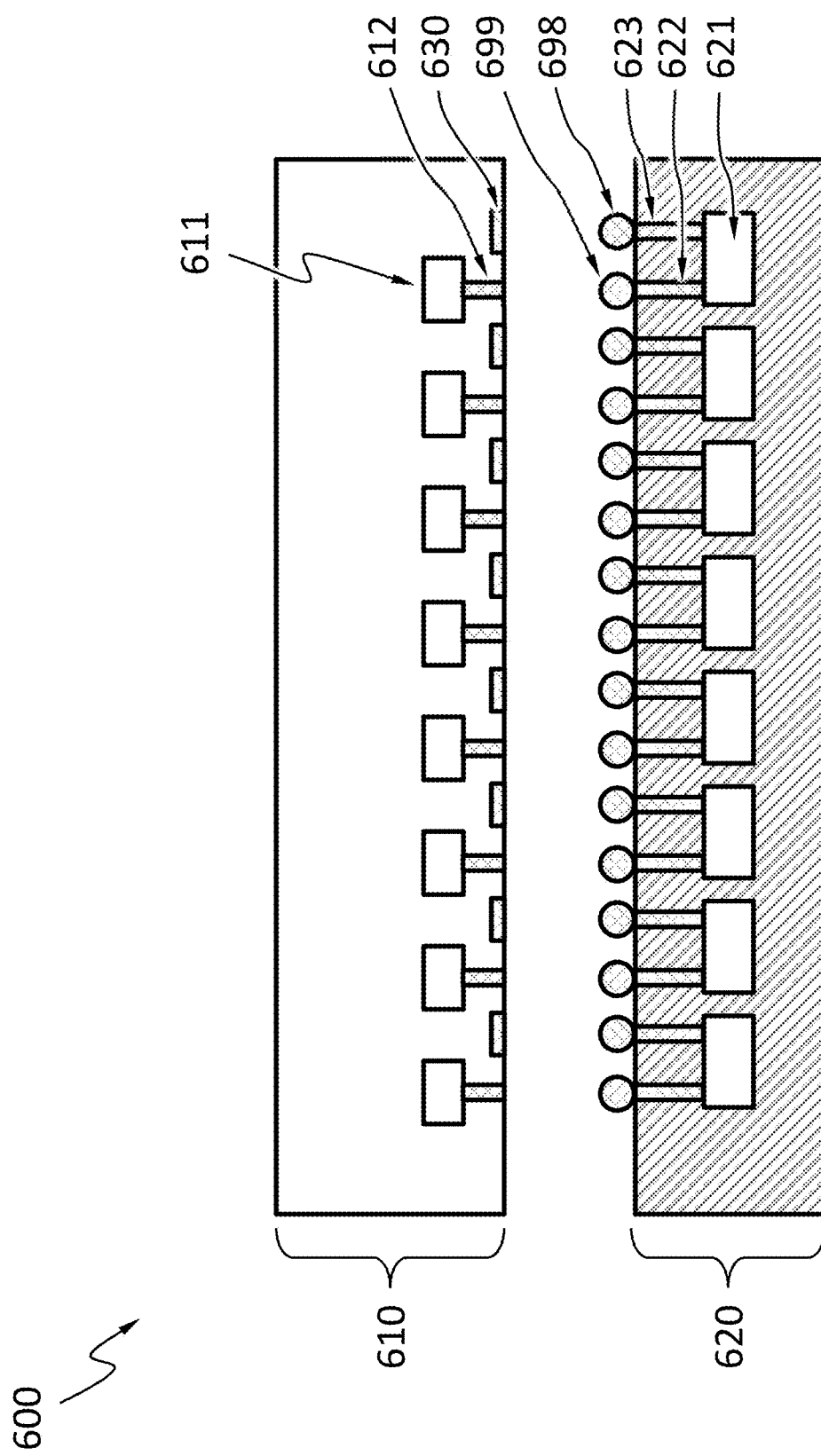
FIG. 5A and FIG. 5B schematically show a cross-sectional view of a radiation detector comprising a plurality of APDs.
Figure 5B:
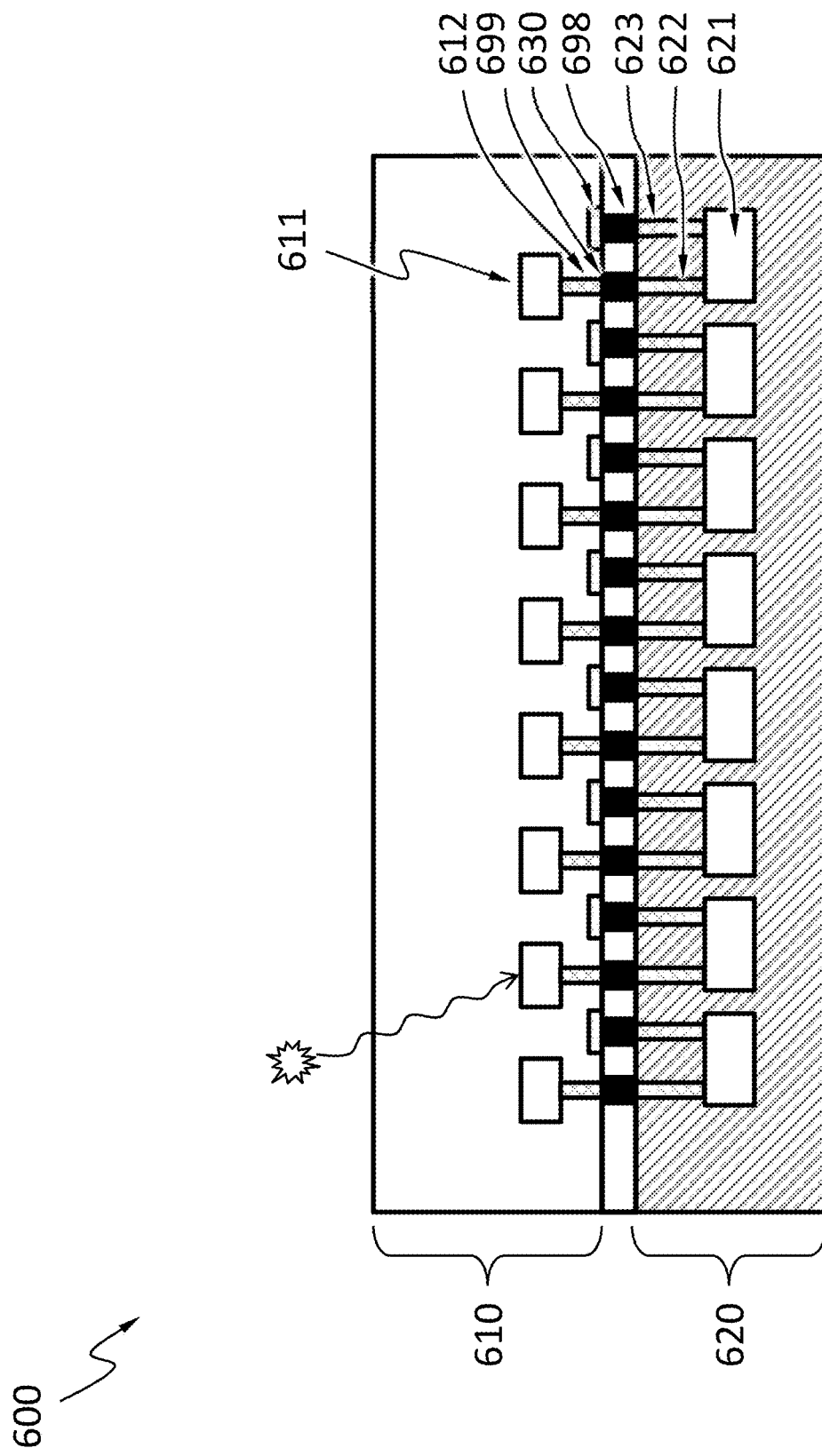

FIG. 5A and FIG. 5B schematically show a cross-sectional view of a radiation detector 600 comprising a plurality of APDs 611. The APDs 611 may be fabricated in a substrate 610 (e.g., a semiconductor wafer). One or more vias 612 may be present in the substrate 610 and the vias 612 electrically connect the APDs 611 to a surface of the substrate 610. Alternatively, the APDs 611 may be disposed on the surface of the substrate 610 such that electrical contacts on the APDs 611 are exposed to the surface. The substrate 610 may include transmission lines 630. Electronic systems 621 that communicate and/or control the APDs 611 may be fabricated in another substrate 620. Electronic systems 621 may include controllers, bias sources, switches, current meters, memories, amplifiers or other suitable components. Some components of the electronic systems 621 may be fabricated in the substrate 610. Electronic systems 621 may be configured to use the APDs 611 using the method illustrated in FIG. 3. One or more vias 622 and 623 may be present and electrically connect the electronic systems 621 to a surface of the substrate 620. Alternatively, the electronic systems 621 may be disposed at the surface of the substrate 620 such that electrical contacts on the electronic systems 621 are exposed to the surface. The substrates 610 and 620 may be bonded by a suitable substrate bonding technique, such as flip chip bonding or direct bonding.

As shown in FIG. 5A and FIG. 5B, flip chip bonding uses solder bumps 699 and 698 deposited onto the surface of either one of the substrates 610 and 620. Either of the substrates 610 and 620 is flipped over and the APDs 611 and the electronic systems 621 are aligned (e.g., through the vias 612, 622 or both). The substrates 610 and 620 are brought into contact. The solder bumps 699 may be melted to electrically connect the APDs 611 and the electronic systems 621. The solder bumps 698 may be melted to electrically connect the electronic systems 621 to the transmission lines 630. The transmission lines 630 configured to transmit data, power and/or signals to and from the electronic systems 621, and through which to and from the APDs 611. Any void space among the solder bumps 699 and 698 may be filled with an insulating material.

It should be noted that the APDs in a radiation detector according to an embodiment (e.g., the radiation detector 300, 500 and/or 600) may work in the linear mode. The signals generated by the radiation incident on the radiation absorption layer (e.g., 210 or 311) may be in a form of an electrical current. Likewise, the dark noise may also be in a form of an electrical current (e.g., a DC current or leakage current flowing from the electric contacts 219B or electrodes 304). If the current may be ascertained, the electrical current may be compensated for (e.g., diverted from) the electronic system (e.g., 221, 521 or 621).

Figure 6A:
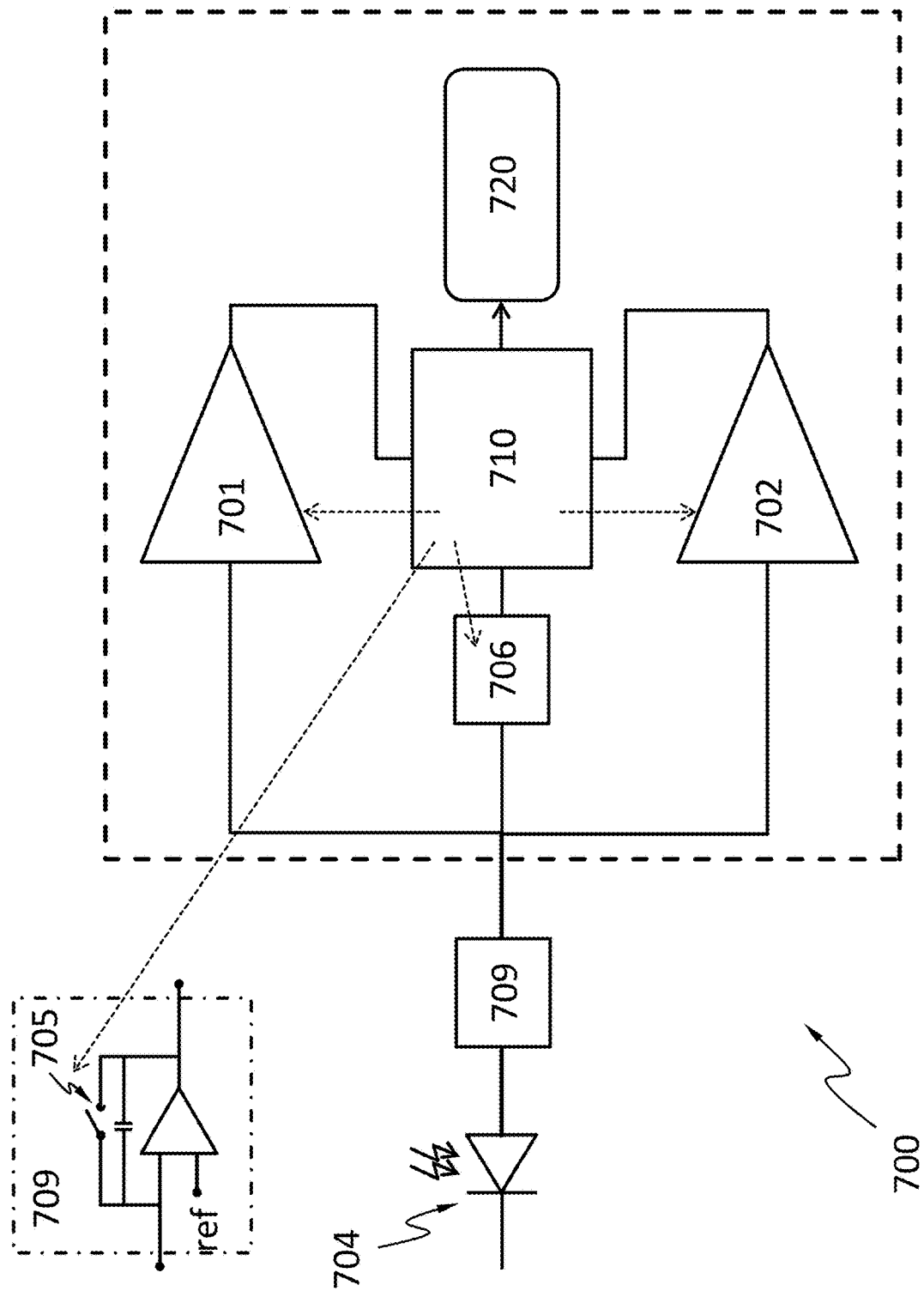
FIG. 6A and FIG. 6B each show a component diagram of an electronic system of a radiation detector, according to an embodiment.
Figure 6B:
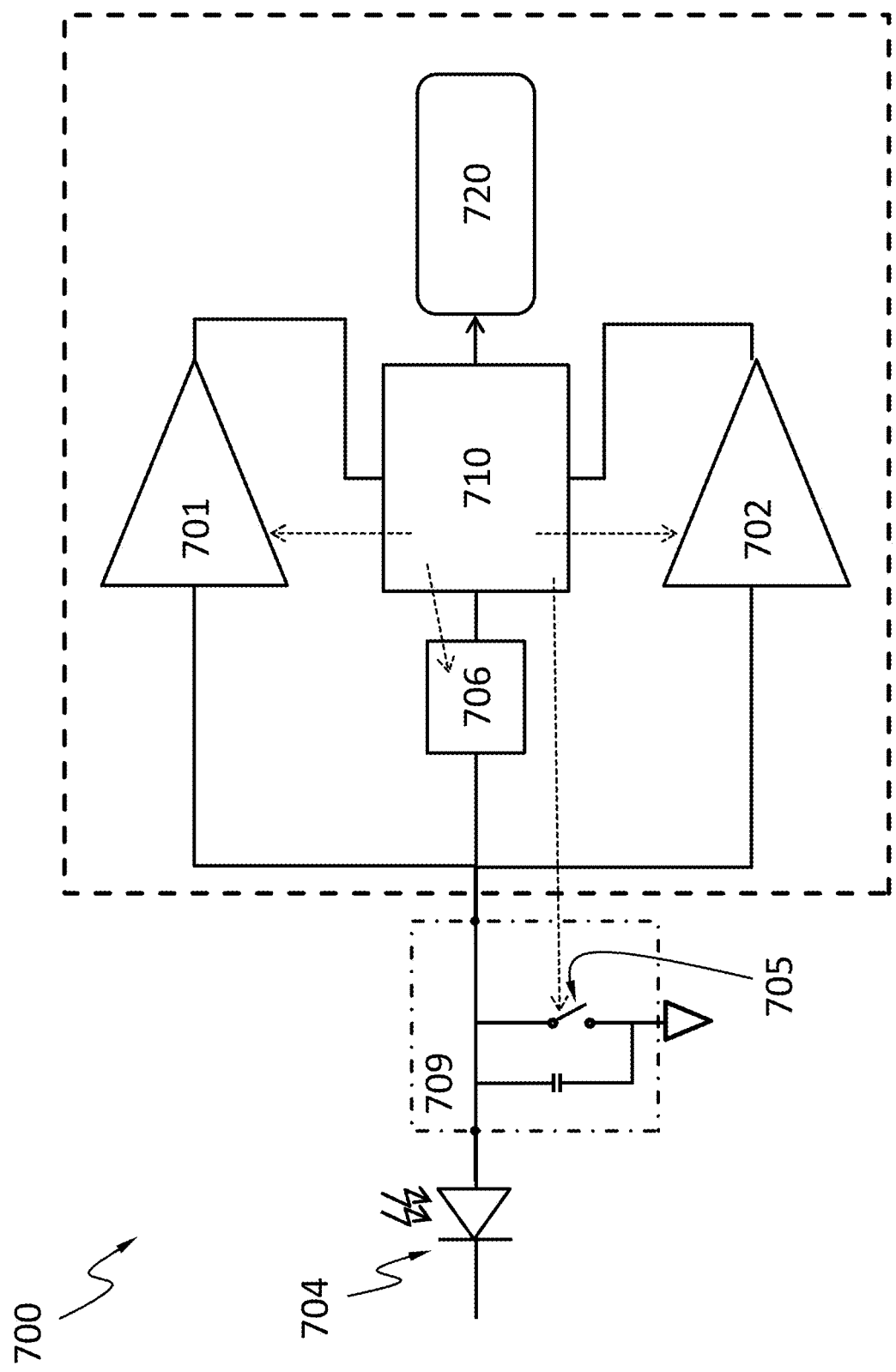

FIG. 6A and FIG. 6B each show a component diagram of the electronic system 700 according to an embodiment. The system 700 may be any one of the electronic systems described herein, for example, 221, 521 or 621. The system includes a capacitor module 709 electrically connected to an electrode of a diode 704 or an electrical contact, wherein the capacitor module is configured to collect charge carriers from the electrode. The diode 704 may be an exemplary APD as described herein and the electrical contact may be an electrical contact of an exemplary APD as described herein. The capacitor module can include a capacitor and charge carriers from the electrode accumulate on the capacitor over a period of time ("integration period"). After the integration period has expired, the capacitor voltage is sampled and then reset by a reset switch. The capacitor module can include a capacitor directly connected to the electrode. The capacitor may be in the feedback path of an amplifier. The amplifier configured as such is called a capacitive transimpedance amplifier (CTIA). CTIA has high dynamic range by keeping the amplifier from saturating and improves the signal-to-noise ratio by limiting the bandwidth in the signal path.

The dark noise in the form of an electrical current, if not compensated for, charges the capacitor in the capacitor module 709 along with the signals generated by the radiation.

Figure 7A:
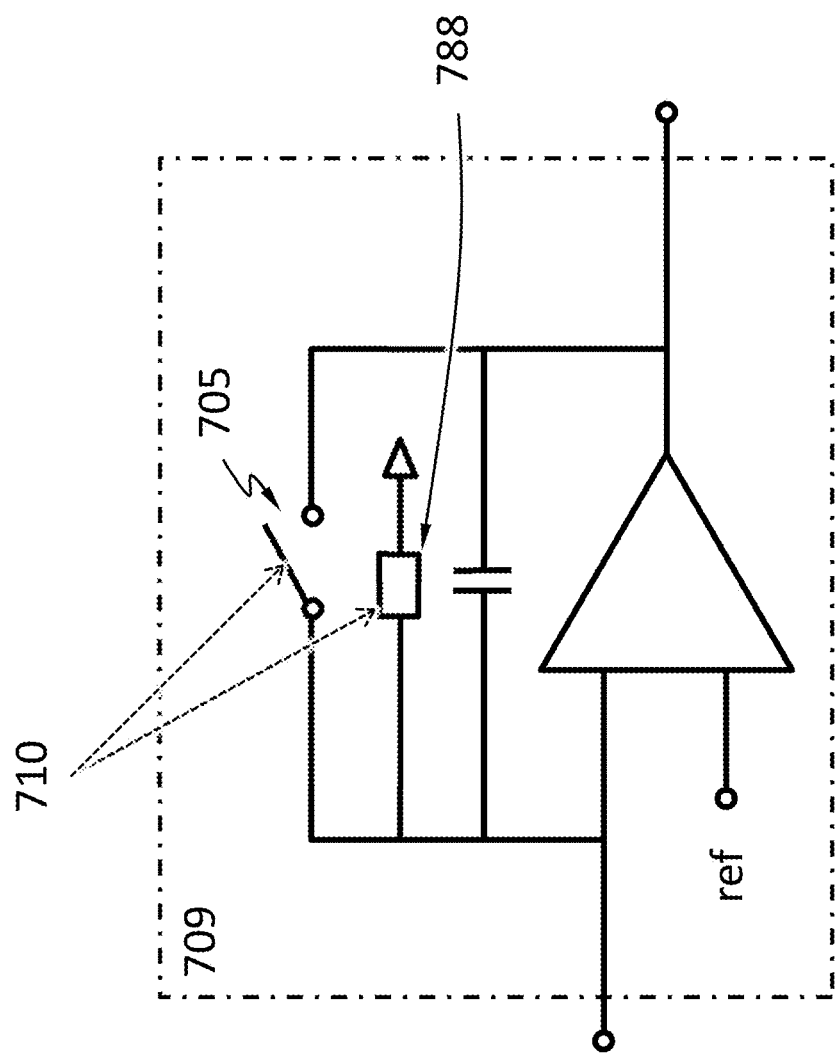
FIG. 7A and FIG. 7B respectively show a circuit configured to compensate for the dark noise in the form of an electrical current.
Figure 7B:
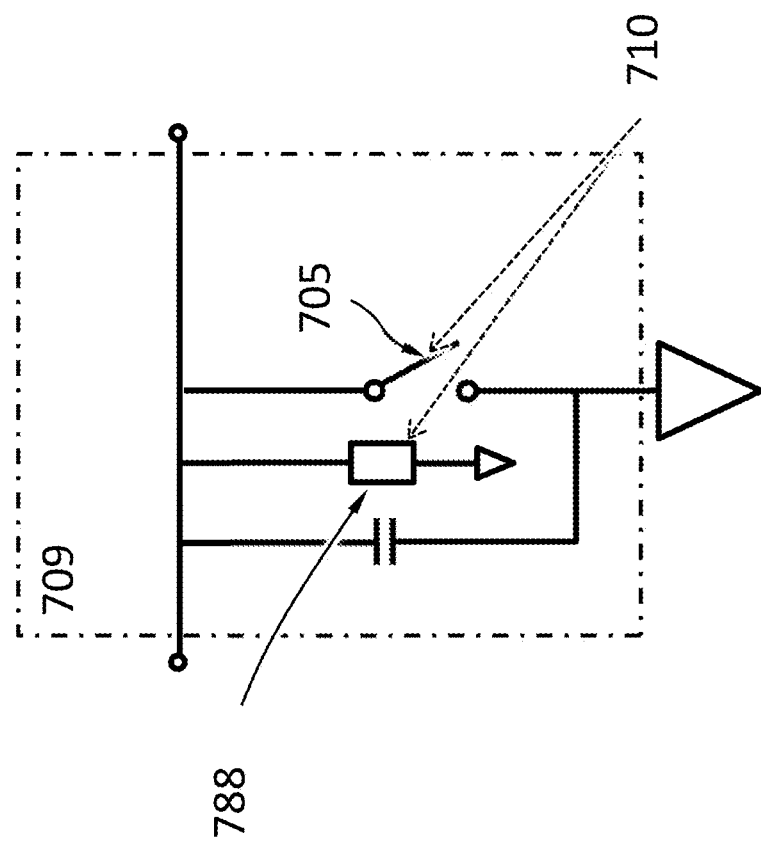

FIG. 7A and FIG. 7B respectively show a circuit configured to provide an electrical current to compensate for the dark noise. Dark noise in the semiconductor devices may include leakage current in the semiconductor materials, for example, leakage current in an APD. A current sourcing module 788 is in parallel to the capacitor. The current sourcing module 788 may be adjustable such that the electrical current it sources compensates for the electrical current of the dark noise. In the circuit shown in FIG. 7A and FIG. 7B, the electrical current of the dark noise is diverted through the current sourcing module 788 so that the electrical current of the dark noise does not charge the capacitor.

Figure 8:
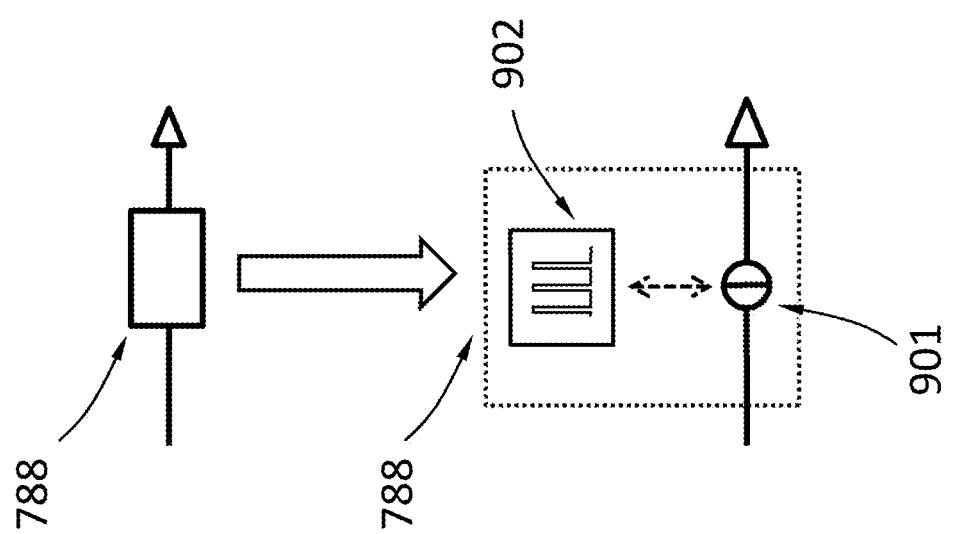
FIG. 8 schematically shows the current sourcing module in the electronic system of the radiation detector, according to an embodiment.

The electrical current of the dark noise may be a very small current, such as in the range of picoamps (e.g., 1-1000 pA). Compensating for a small electrical current may be challenging. FIG. 8 schematically shows the current sourcing module 788, according to an embodiment. The current sourcing module 788 may include a current source 901 and a modulator 902. The current source 901 is configured to output a first electrical current and a second electrical current. The first electrical current and the second electrical current are different in their magnitude, direction, or both. The modulator 902 controls the ratio of the duration at which the current source 901 outputs the first electrical current to the duration at which the current source 901 outputs the second electrical current. The first electrical current and the second electrical current may not be as small as the electrical current of the dark noise but the temporal average of the electrical current the current sourcing module 788 sources, as a result of the modulation by the modulator 902, may be equal to the electrical current of the dark noise. For example, at least one of the first electrical current and the second electrical current is at least an order of magnitude larger than the electrical current of the dark noise. For example, if the first electrical current is 1 nA and the second electrical current is 0, and the ratio is 1:999, the temporal average of the electrical current the current sourcing module 788 sources is 1 pA. The modulator 902 may be as simple as a switch. The modulator 902 may have complex circuitry such as a processor or a memory.

Figure 10:
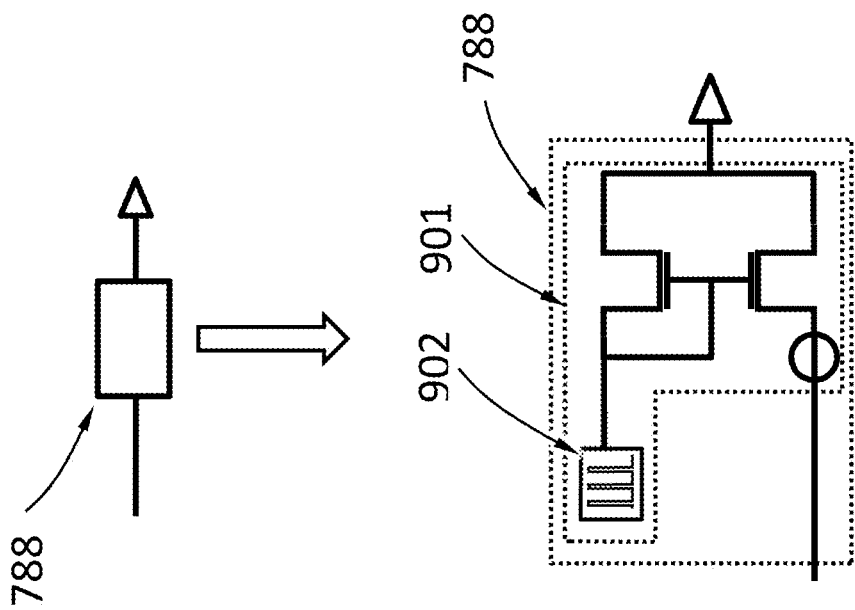
FIG. 9 and FIG. 10 show two examples of the current sourcing module, where the current source of the current sourcing module includes a current mirror.
Figure 9:
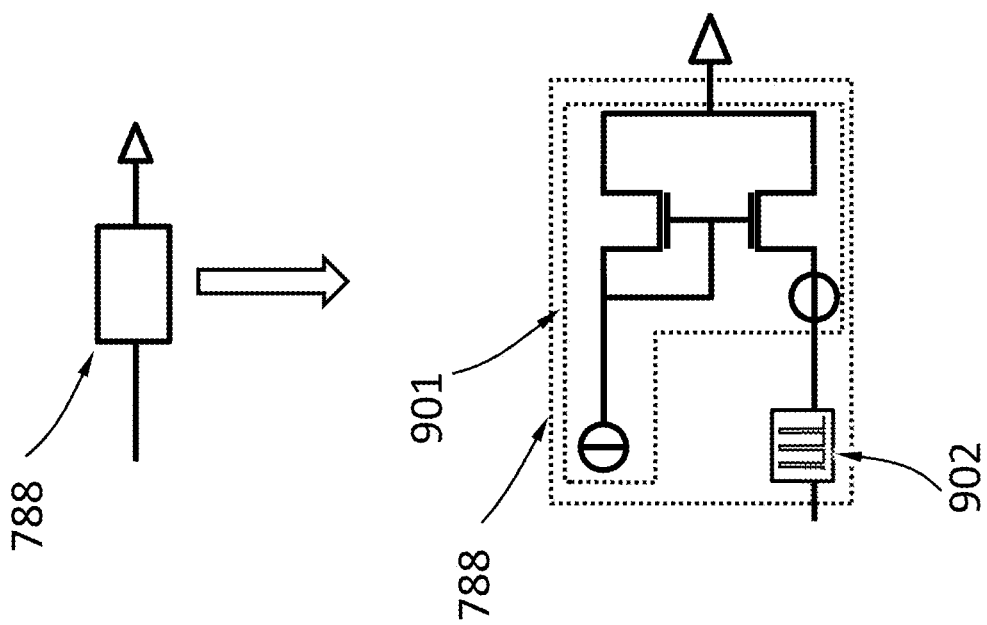

FIG. 9 and FIG. 10 show two examples of the current sourcing module 788, where the current source 901 includes a current mirror. A current mirror is a circuit that receives an input electrical current and outputs an output electrical current proportional to the input electrical current. A current mirror can be viewed as a current-controlled current source (CCCS). A current mirror may include two cascaded current-to-voltage and voltage-to-current converters placed at the same conditions and having reverse characteristics. A current mirror may be implemented using MOSFET transistors as shown here. A current mirror may be implemented using bipolar junction transistors. The modulator 902 may be located on the output stage of the current mirror, as shown in FIG. 9. For example, the modulator 902 may include a switch that controllably connects the current sourcing module 788 to and disconnects it from the capacitor in the capacitor module 709. The modulator 902 may be located on the input stage of the current mirror, as shown in FIG. 10. The modulator 902 may include a current source outputting electrical current at alternating magnitudes. The modulator 902 may include a current source outputting two magnitudes of electrical current with adjustable ratio of durations.

Figure 11:
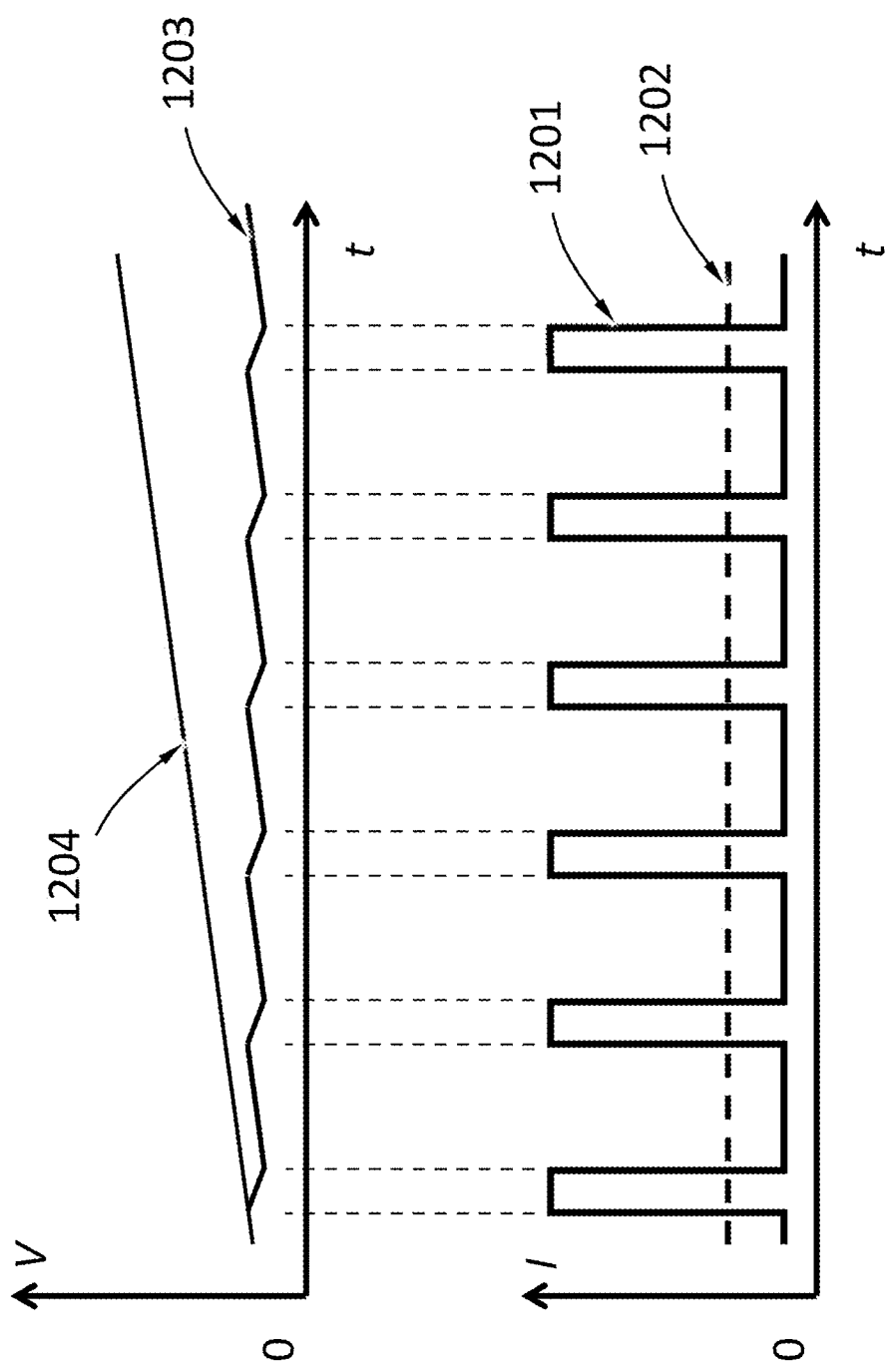
FIG. 11 schematically shows the electrical current the current sourcing module sources, the voltage across the capacitor of the capacitor module attributable to the dark noise and the electrical current the current sourcing module provides, the voltage across the capacitor of the capacitor module attributable to only the dark noise, as functions of time.

FIG. 11 schematically shows an electrical current 1201 of the current sourcing module 788 sources, as a function of time. The dashed line 1202 shows the temporal average of the electrical current 1201. FIG. 11 also schematically shows the voltage 1203 across the capacitor of the capacitor module 709 attributable to the dark noise and the electrical current the current sourcing module 788 provides, as a function of time. FIG. 11 also schematically shows the voltage 1204 across the capacitor of the capacitor module 709 attributable to only the dark noise, as a function of time. It can be observed from FIG. 11 that the electrical current the current sourcing module 788 provides, on temporal average, removes the effect of the dark noise on the voltage across the capacitor.

Figure 12:
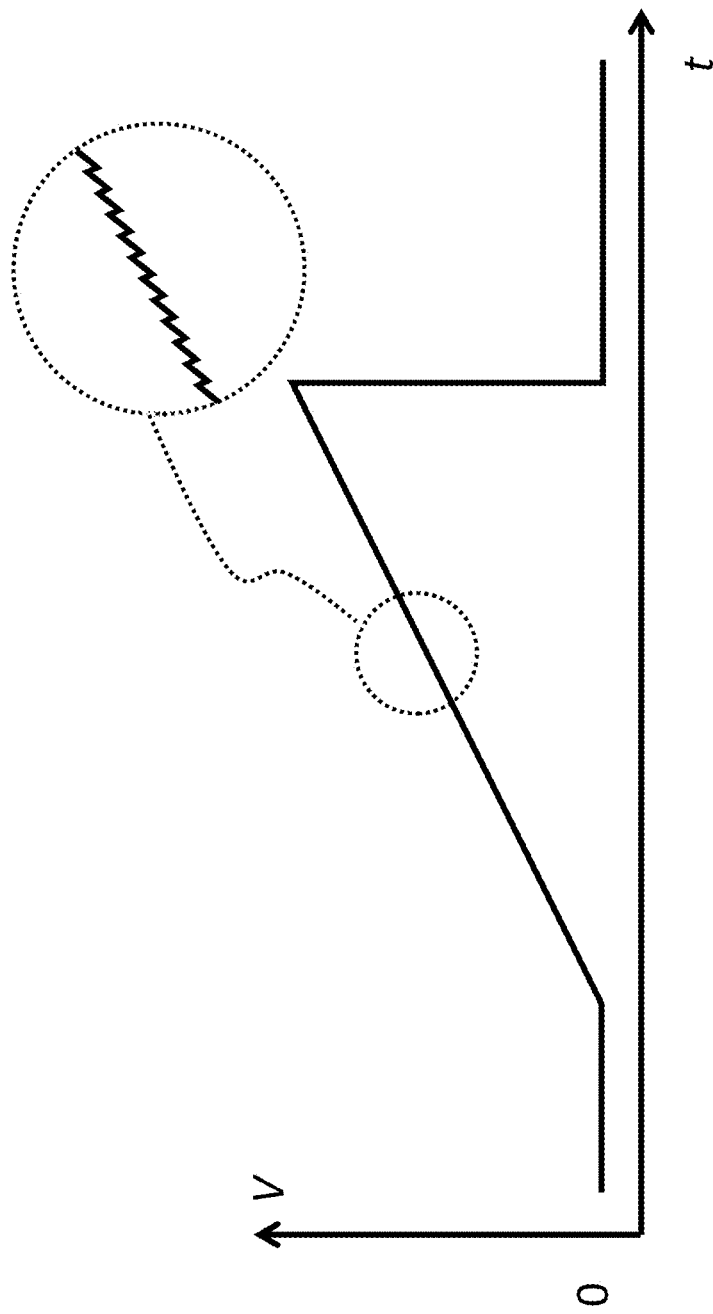
FIG. 12 schematically shows a voltage across the capacitor as a function of time, where the capacitor module includes the current sourcing module.

FIG. 12 schematically shows a voltage across the capacitor as a function of time, where the capacitor module 709 includes the current sourcing module 788. A fine saw tooth waveform superimposed on a smoothly changing voltage can be seen in FIG. 12. The saw tooth waveform is attributable to the dark noise and the electrical current the current sourcing module 788 provides, as a function of time.

FIG. 13 schematically shows a flow chart for a method of compensating for dark noise in a radiation detector. In procedure 2010, a contribution 2020 of a dark noise in the signals of the radiation detector is determined. For example, the contribution may be determined by measuring the signals while the radiation detector receives no radiation. In procedure 2030, a ratio 2040 of a duration of a first compensatory signal 2050 to a duration of a second compensatory signal 2060 is determined based on the contribution 2020 of the dark noise, the first compensatory signal 2050 and the second compensatory signal 2060. For example, the first compensatory signal 2050 and the second compensatory signal 2060 may be the first electrical current and the second electrical current output by the current source 901. In procedure 2070, the signals of the radiation detector are compensated for the dark noise with the first compensatory signal 2050 and the second compensatory signal 2060 with their respective durations with the ratio 2040.

Figure 14A:
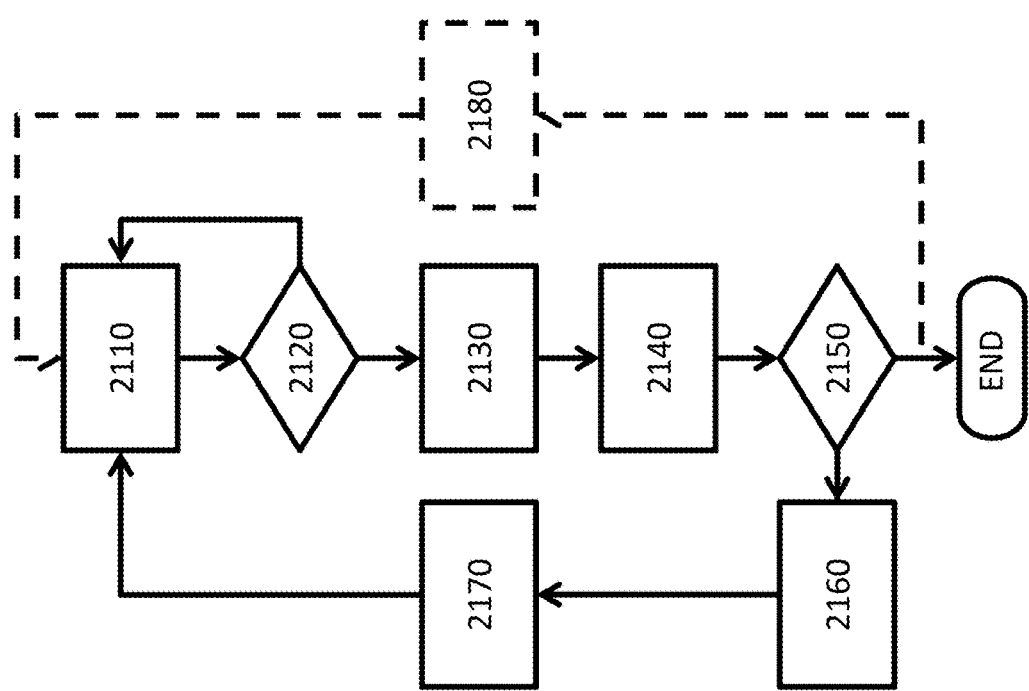
FIG. 14A schematically shows a flow chart for a method of compensating for dark noise in a radiation detector.

FIG. 14A schematically shows a flow chart for a method of compensating for dark noise in a radiation detector. In procedure 2110, signals of the radiation detector are measured, when the radiation detector receives no radiation and a compensation for the dark noise of the radiation detector is present. In procedure 2120, if the signals have not exceeded a first level, the flow goes back the procedure 2110; if the signals have exceeded the first level, a time delay is commenced in procedure 2130. In procedure 2140, the signals of the radiation detector at the end of the time delay are measured. In procedure 2150, if the signals do not exceed a second level, the flow ends and the current magnitude of compensation is deemed sufficient to compensate for the contribution of the dark noise; if the signals at the end of the time delay exceed the second level, the compensation for the dark noise is increased in procedure 2160, the signals are reset in procedure 2170, and the flow goes back the procedure 2110. Alternatively, in procedure 2150, if the signals do not exceed a second level, the second level is lowered in procedure 2180 and the flow goes back the procedure 2110; if the signals at the end of the time delay exceed the second level, the compensation for the dark noise is increased in procedure 2160, the signals are reset in procedure 2170, and the flow goes back the procedure 2110. When the compensation for the dark noise is increased, it may be increased to a magnitude among a group of discrete values. The current magnitude of compensation may be stored in a memory in the radiation detector.

FIG. 14B schematically shows a flow chart for a method of compensating for dark noise in a radiation detector. In procedure 2210, signals of the radiation detector are measured, when the radiation detector receives no radiation and a compensation for the dark noise of the radiation detector is present. In procedure 2220, if the signals have not exceeded a first level, the flow goes back the procedure 2210; if the signals have exceeded the first level, a time delay is commenced in procedure 2230. In procedure 2240, if the signals of the radiation detector at the end of the time delay are measured. In procedure 2250, the difference of the signals at the beginning of the time delay (which may simply be the first level) and the signals at the end of the time delay is determined. In procedure 2260, the magnitude of the compensation for the dark noise is determined based on the difference.

In addition the capacitor module 709, which includes the current sourcing module 788, the electronic system 700 may further include a first voltage comparator 701, a second voltage comparator 702, a counter 720, a switch 705, a voltmeter 706 and a controller 710, as shown in FIG. 6A and FIG. 6B.

The first voltage comparator 701 is configured to compare the voltage of an electrode of a diode 704 to a first threshold. The diode may be an APD as described herein. Alternatively, the first voltage comparator 701 is configured to compare the voltage of an electrical contact (e.g., a discrete portion of electrical contact 219B) to a first threshold. The first voltage comparator 701 may be configured to monitor the voltage directly, or calculate the voltage by integrating an electric current flowing through the diode or electrical contact over a period of time. The first voltage comparator 701 may be controllably activated or deactivated by the controller 710. The first voltage comparator 701 may be a continuous comparator. Namely, the first voltage comparator 701 may be configured to be activated continuously, and monitor the voltage continuously. The first voltage comparator 701 configured as a continuous comparator reduces the chance that the system 700 misses signals generated by an incident photon. The first voltage comparator 701 configured as a continuous comparator is especially suitable when the incident radiation intensity is relatively high. The first voltage comparator 701 may be a clocked comparator, which has the benefit of lower power consumption. The first voltage comparator 701 configured as a clocked comparator may cause the system 700 to miss signals generated by some incident photons. When the incident radiation intensity is low, the chance of missing an incident photon is low because the time interval between two successive photons is relatively long. Therefore, the first voltage comparator 701 configured as a clocked comparator is especially suitable when the incident radiation intensity is relatively low. The first threshold may be 5-10%, 10%-20%, 20-30%, 30-40% or 40-50% of the maximum voltage one incident photon may generate in the APD. The maximum voltage may depend on the energy of the incident photon (i.e., the wavelength of the incident radiation), the material of the radiation absorption layer, and other factors. For example, the first threshold may be 50 mV, 100 mV, 150 mV, or 200 mV.

The second voltage comparator 702 is configured to compare the voltage to a second threshold. The second voltage comparator 702 may be configured to monitor the voltage directly, or calculate the voltage by integrating an electric current flowing through the diode or the electrical contact over a period of time. The second voltage comparator 702 may be a continuous comparator. The second voltage comparator 702 may be controllably activate or deactivated by the controller 710. When the second voltage comparator 702 is deactivated, the power consumption of the second voltage comparator 702 may be less than 1%, less than 5%, less than 10% or less than 20% of the power consumption when the second voltage comparator 702 is activated. The absolute value of the second threshold is greater than the absolute value of the first threshold. As used herein, the term "absolute value" or "modulus" |x| of a real number x is the non-negative value of x without regard to its sign. Namely, $$|x| = \begin{cases} x, \text{ if } x \geq 0 \\ -x, \text{ if } x \leq 0 \end{cases}.$$

The second threshold may be 200%-300% of the first threshold. The second threshold may be at least 50% of the maximum voltage one incident X-ray photon may generate in the diode or resistor. For example, the second threshold may be 100 mV, 150 mV, 200 mV, 250 mV or 300 mV. The second voltage comparator 702 and the first voltage comparator 701 may be the same component. Namely, the system 700 may have one voltage comparator that can compare a voltage with two different thresholds at different times.

The first voltage comparator 701 or the second voltage comparator 702 may include one or more op-amps or any other suitable circuitry. The first voltage comparator 701 or the second voltage comparator 702 may have a high speed to allow the system 700 to operate under a high flux of incident X-ray. However, having a high speed is often at the cost of power consumption.

The counter 720 is configured to register a number of X-ray photons reaching the diode or resistor. The counter 720 may be a software component (e.g., a number stored in a computer memory) or a hardware component (e.g., a 4017 IC and a 7490 IC).

The controller 710 may be a hardware component such as a microcontroller and a microprocessor. The controller 710 is configured to start a time delay from a time at which the first voltage comparator 701 determines that the absolute value of the voltage equals or exceeds the absolute value of the first threshold (e.g., the absolute value of the voltage increases from below the absolute value of the first threshold to a value equal to or above the absolute value of the first threshold). The absolute value is used here because the voltage may be negative or positive, depending on whether the voltage of the cathode or the anode of the diode or which electrical contact is used. The controller 710 may be configured to keep deactivated the second voltage comparator 702, the counter 720 and any other circuits the operation of the first voltage comparator 701 does not require, before the time at which the first voltage comparator 701 determines that the absolute value of the voltage equals or exceeds the absolute value of the first threshold. The time delay may expire before or after the voltage becomes stable, i.e., the rate of change of the voltage is substantially zero. The phase "the rate of change of the voltage is substantially zero" means that temporal change of the voltage is less than 0.1%/ns. The phase "the rate of change of the voltage is substantially non-zero" means that temporal change of the voltage is at least 0.1%/ns.

The controller 710 may be configured to activate the second voltage comparator during (including the beginning and the expiration) the time delay. In an embodiment, the controller 710 is configured to activate the second voltage comparator at the beginning of the time delay. The term "activate" means causing the component to enter an operational state (e.g., by sending a signal such as a voltage pulse or a logic level, by providing power, etc.). The term "deactivate" means causing the component to enter a non-operational state (e.g., by sending a signal such as a voltage pulse or a logic level, by cut off power, etc.). The operational state may have higher power consumption (e.g., 10 times higher, 100 times higher, 1000 times higher) than the non-operational state. The controller 710 itself may be deactivated until the output of the first voltage comparator 701 activates the controller 710 when the absolute value of the voltage equals or exceeds the absolute value of the first threshold.

The controller 710 may be configured to cause the number registered by the counter 720 to increase by one, if, during the time delay, the second voltage comparator 702 determines that the absolute value of the voltage equals or exceeds the absolute value of the second threshold.

The controller 710 may be configured to cause the voltmeter 706 to measure the voltage upon expiration of the time delay. The controller 710 may be configured to connect the electrode to an electrical ground, so as to reset the voltage and discharge any charge carriers accumulated on the electrode. In an embodiment, the electrode is connected to an electrical ground after the expiration of the time delay. In an embodiment, the electrode is connected to an electrical ground for a finite reset time period. The controller 710 may connect the electrode to the electrical ground by controlling the switch 705. The switch may be a transistor such as a field-effect transistor (FET).

In an embodiment, the system 700 has no analog filter network (e.g., a RC network). In an embodiment, the system 700 has no analog circuitry.

The voltmeter 706 may feed the voltage it measures to the controller 710 as an analog or digital signal.

The controller 710 may be configured to control the current sourcing module 388. For example, the controller 710 may change the magnitude of compensation for the dark noise by controlling the current sourcing module 788. The controller 710 may adjust the ratio 2040 of the duration of the first compensatory signal 2050 to the duration of a second compensatory signal 2060 ratio in the flow of FIG. 13. The controller 710 may execute instructions reside in volatile memory, non-volatile memory, RAM, flash memory, ROM, EPROM, or any other form of a non-transitory computer-readable storage medium and thereby implement the flows of FIG. 13, FIG. 14A and FIG. 14B.

Figure 15:
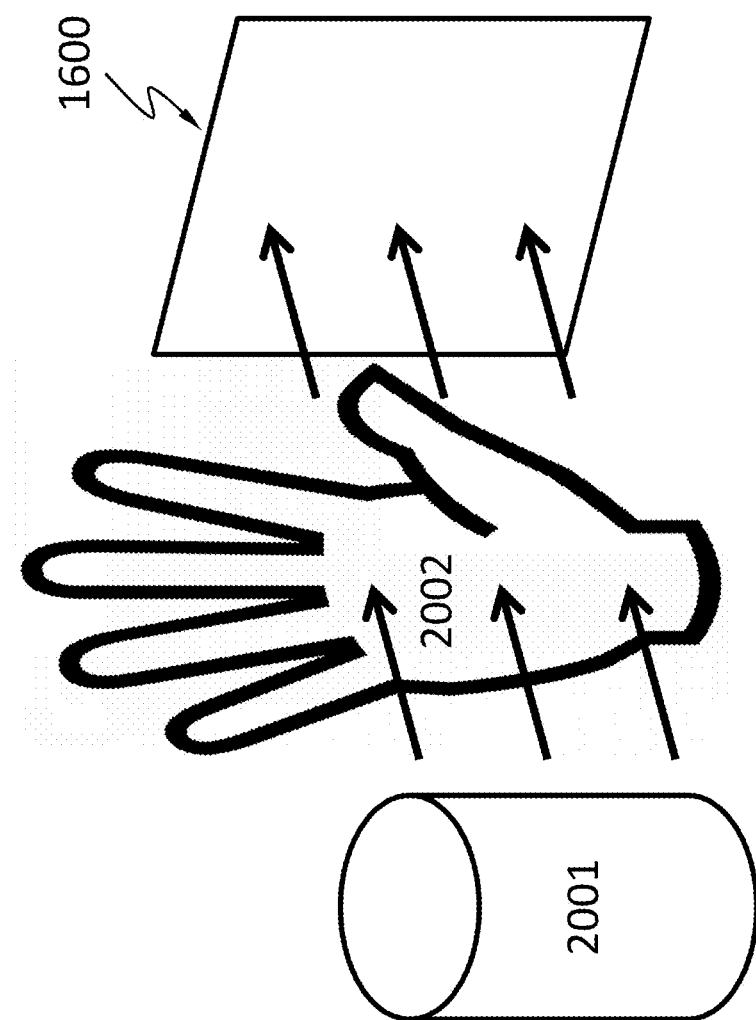
FIG. 15-FIG. 21 each schematically show a system comprising the radiation detector described herein.

FIG. 15 schematically shows a system comprising a radiation detector 1600. The radiation detector 1600 may be one exemplary embodiment of one of the radiation detector described herein. The system may be used for medical imaging such as chest X-ray radiography, abdominal X-ray radiography, etc. The system comprises a pulsed radiation source 2001 that emits X-ray. X-ray emitted from the pulsed radiation source 2001 penetrates an object 2002 (e.g., a human body part such as chest, limb, abdomen), is attenuated by different degrees by the internal structures of the object 2002 (e.g., bones, muscle, fat and organs, etc.), and is projected to the radiation detector 1600. The radiation detector 1600 forms an image by detecting the intensity distribution of the X-ray.

Figure 16:
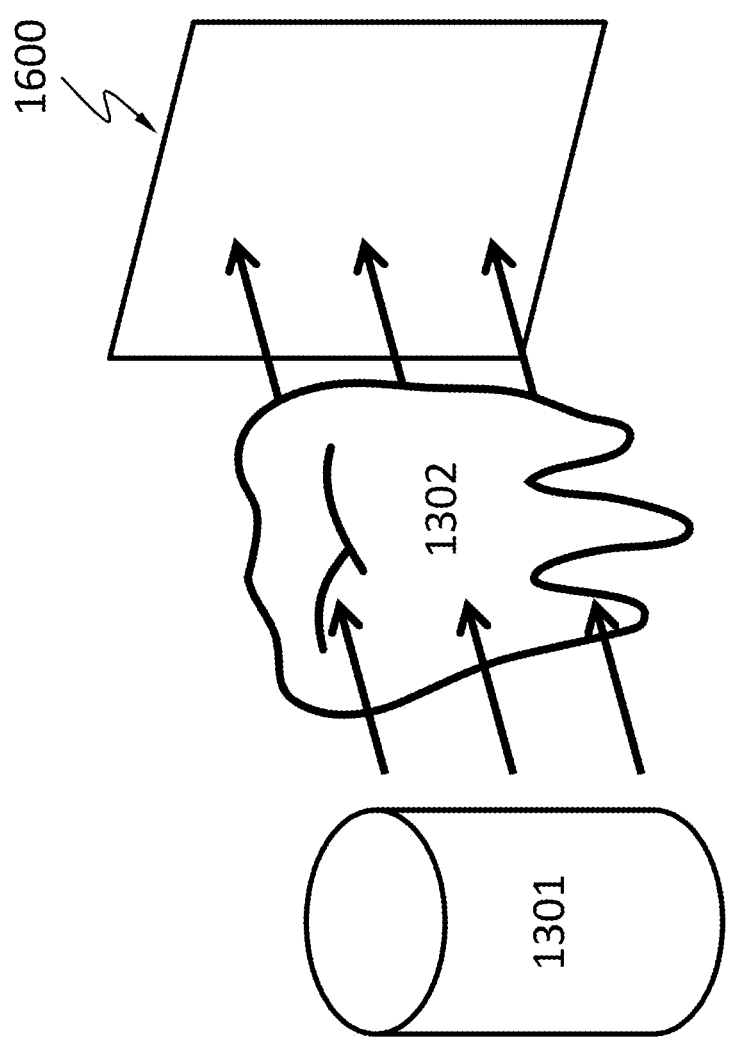

FIG. 16 schematically shows a system comprising the radiation detector 1600 described herein. The system may be used for medical imaging such as dental X-ray radiography. The system comprises a pulsed radiation source 1301 that emits X-ray. X-ray emitted from the pulsed radiation source 1301 penetrates an object 1302 that is part of a mammal (e.g., human) mouth. The object 1302 may include a maxilla bone, a palate bone, a tooth, the mandible, or the tongue. The X-ray is attenuated by different degrees by the different structures of the object 1302 and is projected to the radiation detector 1600. The radiation detector 1600 forms an image by detecting the intensity distribution of the X-ray. Teeth absorb X-ray more than dental caries, infections, periodontal ligament. The dosage of X-ray radiation received by a dental patient is typically small (around 0.150 mSv for a full mouth series).

Figure 17:
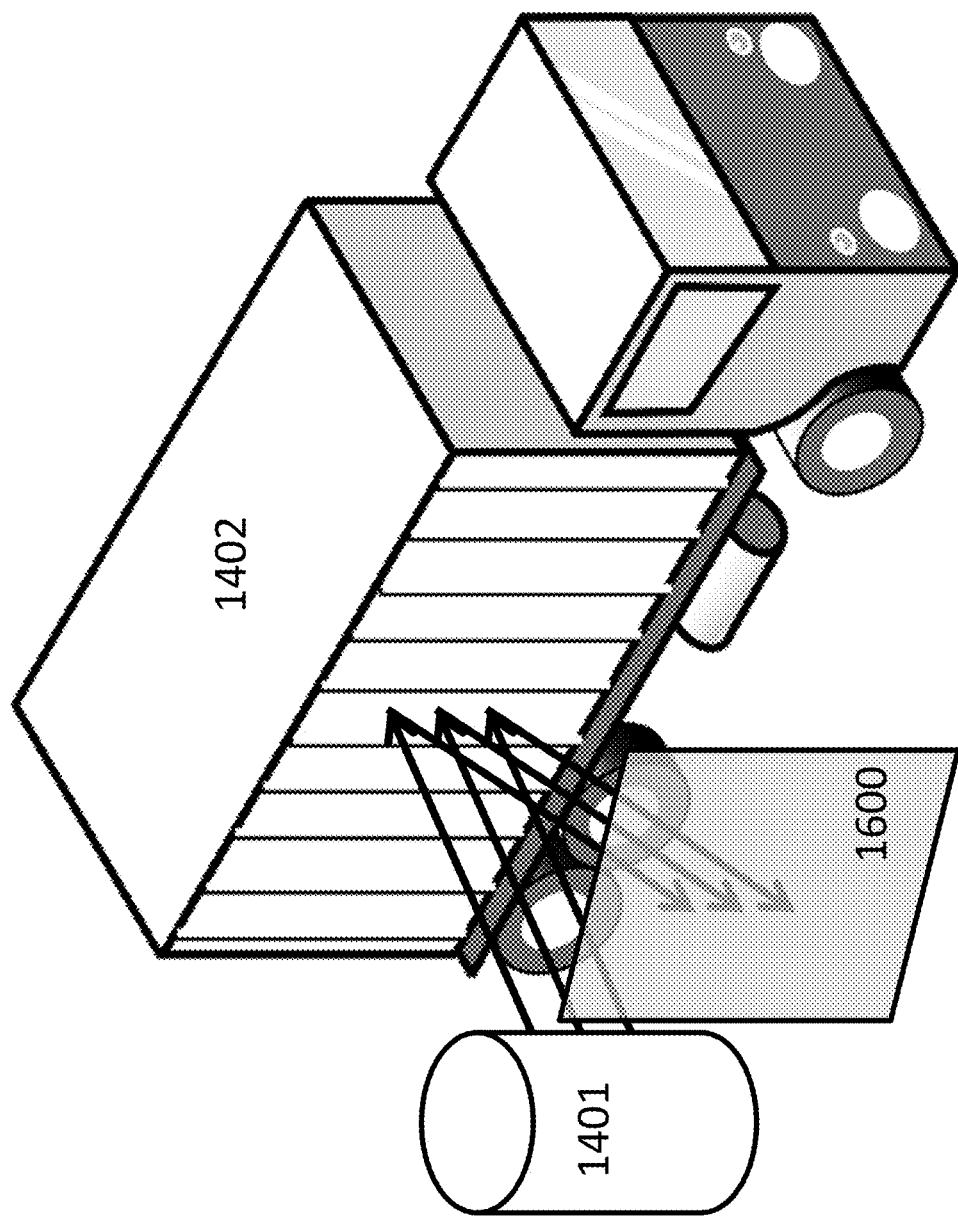

FIG. 17 schematically shows a cargo scanning or non-intrusive inspection (NII) system comprising the radiation detector 1600 described herein. The system may be used for inspecting and identifying goods in transportation systems such as shipping containers, vehicles, ships, luggage, etc. The system comprises a pulsed radiation source 1401.

Radiation emitted from the pulsed radiation source 1401 may backscatter from an object 1402 (e.g., shipping containers, vehicles, ships, etc.) and be projected to the radiation detector 1600. Different internal structures of the object 1402 may backscatter the radiation differently. The radiation detector 1600 forms an image by detecting the intensity distribution of the backscattered radiation and/or energies of the backscattered radiation.

Figure 18:
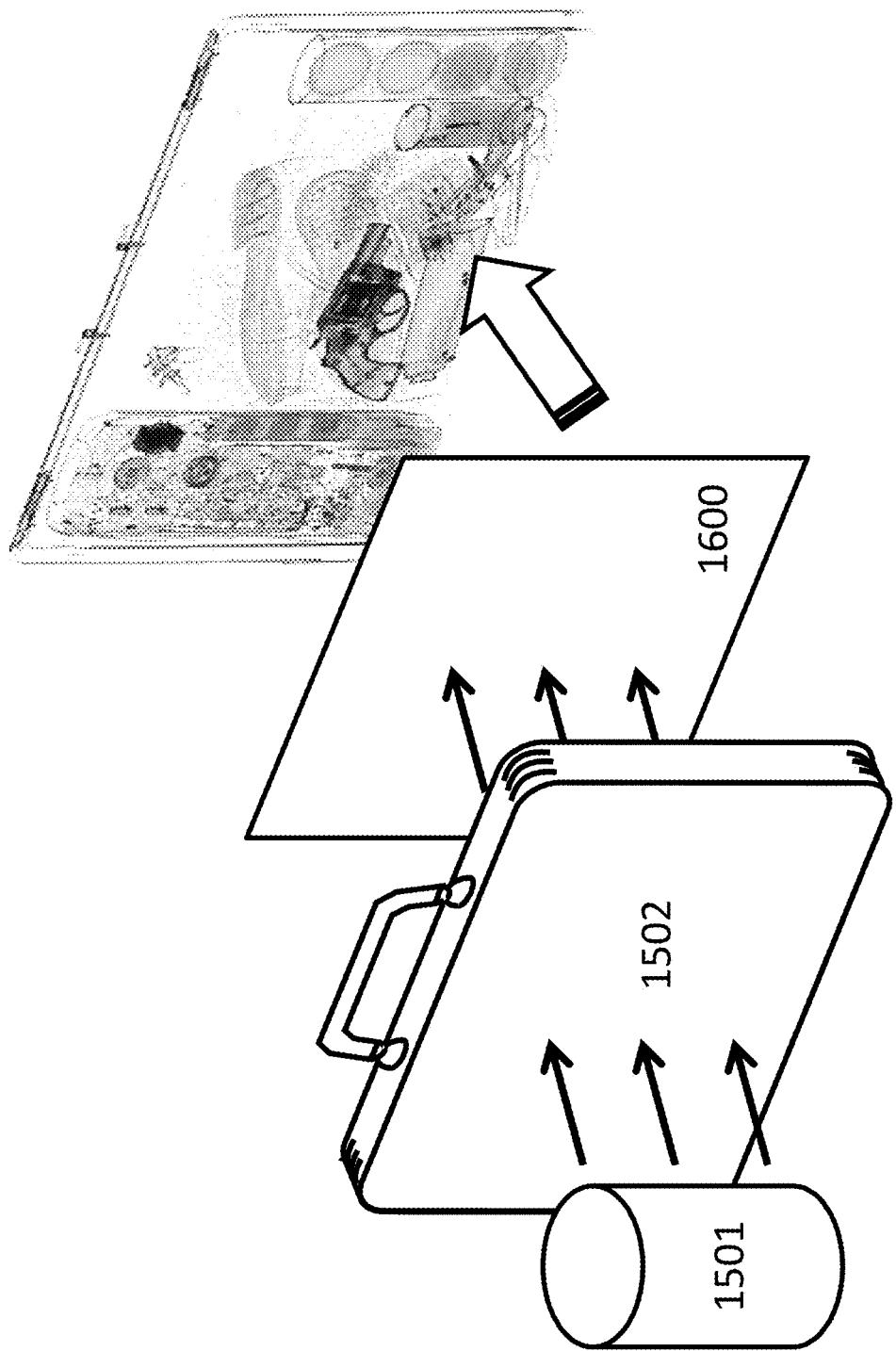

FIG. 18 schematically shows another cargo scanning or non-intrusive inspection (NII) system comprising the radiation detector 1600 described herein. The system may be used for luggage screening at public transportation stations and airports. The system comprises a pulsed radiation source 1501 that emits X-ray. X-ray emitted from the pulsed radiation source 1501 may penetrate a piece of luggage 1502, be differently attenuated by the contents of the luggage, and projected to the radiation detector 1600. The radiation detector 1600 forms an image by detecting the intensity distribution of the transmitted X-ray. The system may reveal contents of luggage and identify items forbidden on public transportation, such as firearms, narcotics, edged weapons, flammables.

Figure 19:
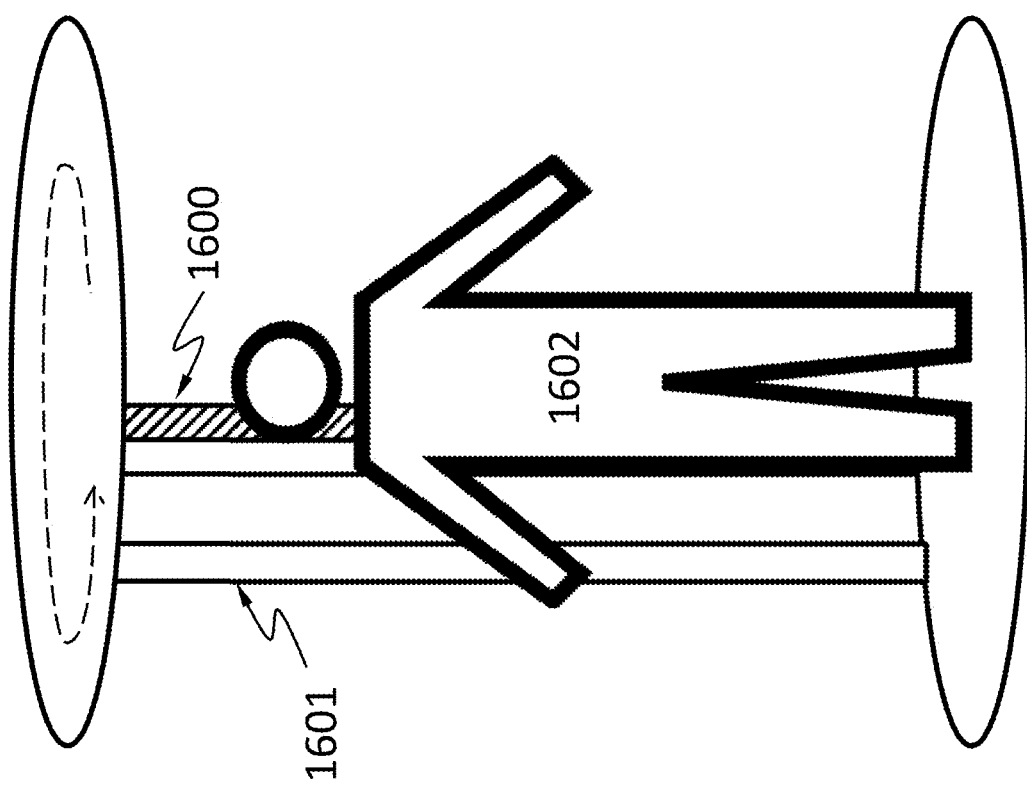

FIG. 19 schematically shows a full-body scanner system comprising the radiation detector 1600 described herein. The full-body scanner system may detect objects on a person's body for security screening purposes, without physically removing clothes or making physical contact. The full-body scanner system may be able to detect non-metal objects. The full-body scanner system comprises a pulsed radiation source 1601. The radiation emitted from the pulsed radiation source 1601 may backscatter from a human 1602 being screened and objects thereon, and be projected to the radiation detector 1600. The objects and the human body may backscatter the radiation differently. The radiation detector 1600 forms an image by detecting the intensity distribution of the backscattered radiation. The radiation detector 1600 and the pulsed radiation source 1601 may be configured to scan the human in a linear or rotational direction.

Figure 20:
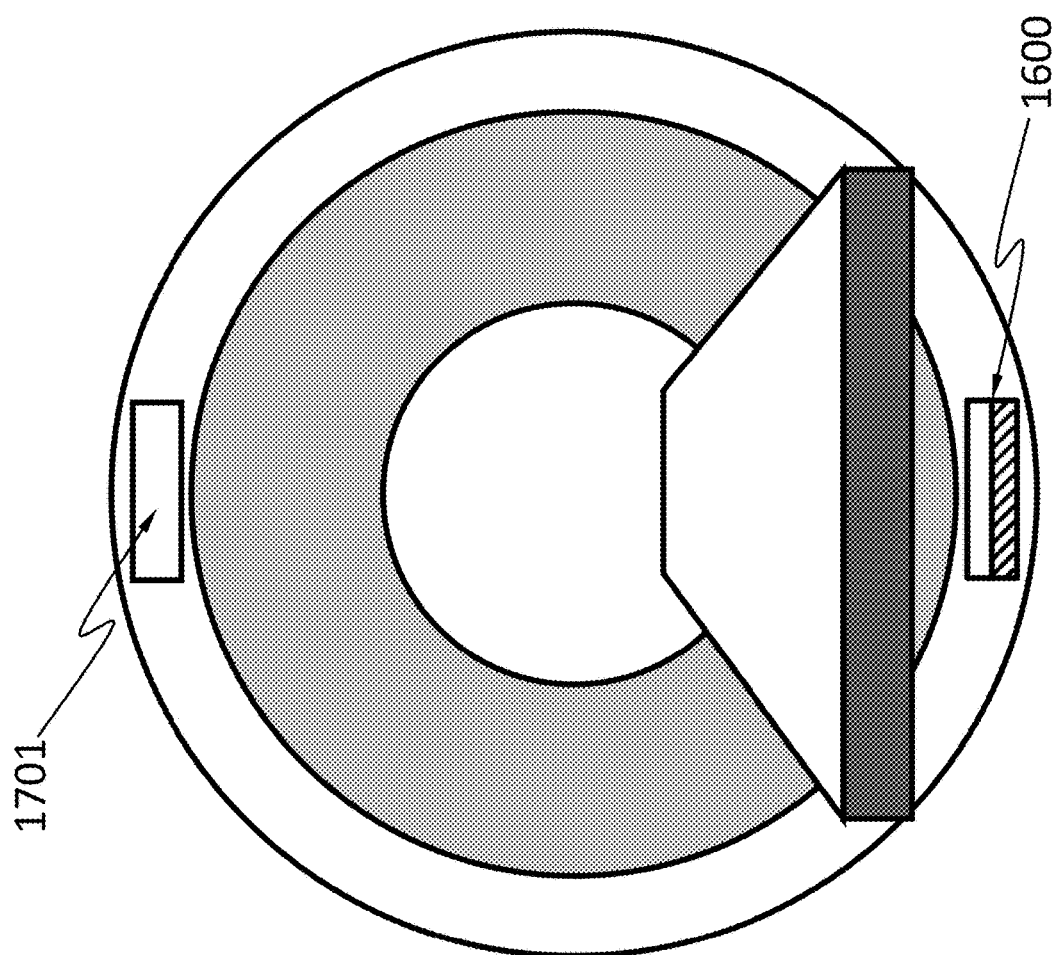

FIG. 20 schematically shows an X-ray computed tomography (X-ray CT) system. The X-ray CT system uses computer-processed X-rays to produce tomographic images (virtual "slices") of specific areas of a scanned object. The tomographic images may be used for diagnostic and therapeutic purposes in various medical disciplines, or for flaw detection, failure analysis, metrology, assembly analysis and reverse engineering. The X-ray CT system comprises the radiation detector 1600 described herein and a pulsed radiation source 1701 that emits X-ray. The radiation detector 1600 and the pulsed radiation source 1701 may be configured to rotate synchronously along one or more circular or spiral paths.

Figure 21:
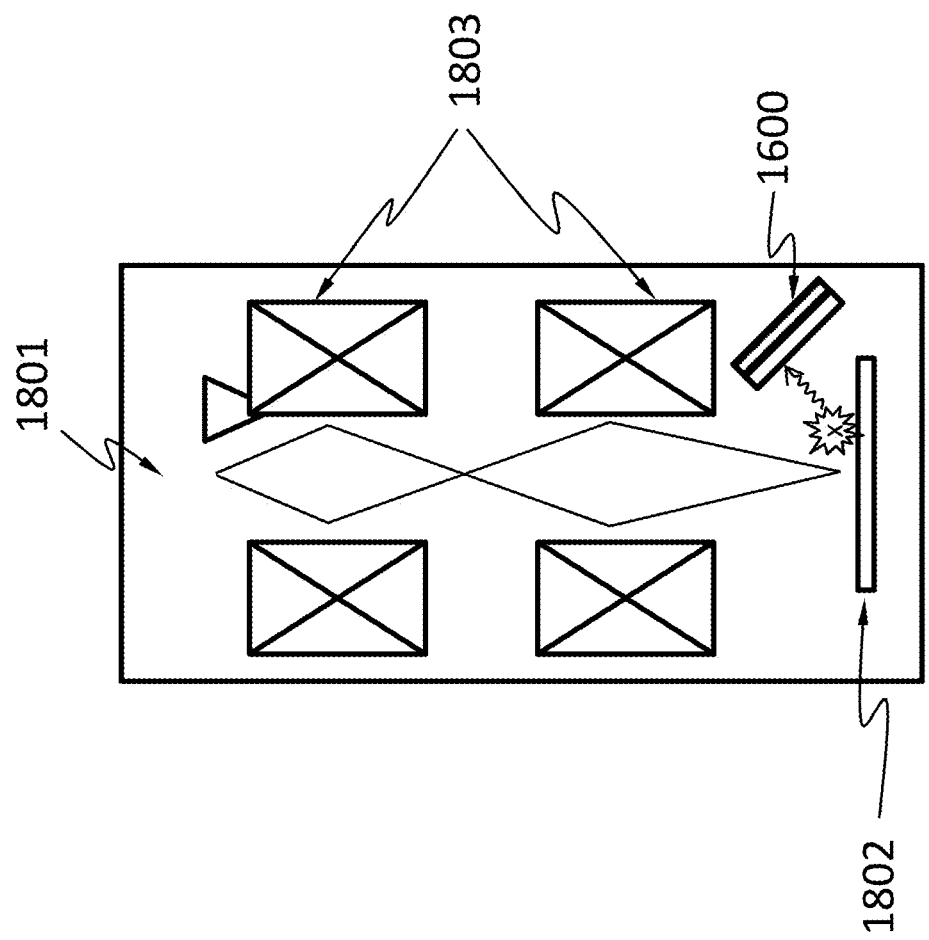

FIG. 21 schematically shows an electron microscope. The electron microscope comprises an electron source 1801 (also called an electron gun) that is configured to emit electrons. The electron source 1801 may have various emission mechanisms such as thermionic, photocathode, cold emission, or plasmas source. The emitted electrons pass through an electronic optical system 1803, which may be configured to shape, accelerate, or focus the electrons. The electrons then reach a sample 1802 and an image detector may form an image therefrom. The electron microscope may comprise the radiation detector 1600 described herein, for performing energy-dispersive X-ray spectroscopy (EDS). EDS is an analytical technique used for the elemental analysis or chemical characterization of a sample. When the electrons incident on a sample, they cause emission of characteristic X-rays from the sample. The incident electrons may excite an electron in an inner shell of an atom in the sample, ejecting it from the shell while creating an electron hole where the electron was. An electron from an outer, higher-energy shell then fills the hole, and the difference in energy between the higher-energy shell and the lower energy shell may be released in the form of an X-ray. The number and energy of the X-rays emitted from the sample can be measured by the radiation detector 1600.

The radiation detector 1600 described here may have other applications such as in an X-ray telescope, X-ray mammography, industrial X-ray defect detection, X-ray microscopy or microradiography, X-ray casting inspection, X-ray non-destructive testing, X-ray weld inspection, X-ray digital subtraction angiography, etc. It may be suitable to use this radiation detector 1600 in place of a photographic plate, a photographic film, a PSP plate, an X-ray image intensifier, a scintillator, or an X-ray detector.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A radiation detector, comprising:
   an avalanche photodiode (APD) with a first side coupled to an electrode and configured to work in a linear mode;
   a current sourcing module configured to compensate for a leakage current in the APD and comprising a current source and a modulator;
   wherein the current source is configured to output a first electrical current and a second electrical current;
   wherein the modulator is configured to control a ratio of a duration at which the current source outputs the first electrical current to a duration at which the current source outputs the second electrical current.

2. The radiation detector of claim 1, wherein the current sourcing module is adjustable.

3. The radiation detector of claim 1, wherein the current sourcing module is configured to divert the leakage current in the APD through the current sourcing module.

4. The radiation detector of claim 1, wherein the first electrical current and the second electrical current are different in their magnitude, direction, or both.

5. The radiation detector of claim 1, wherein least one of the first electrical current and the second electrical current is at least an order of magnitude larger than the leakage current in the APD.

6. The radiation detector of claim 1, wherein the leakage current in the APD is from 1 pA to 1000 pA.

7. The radiation detector of claim 1, wherein the modulator comprises a processor or a memory.

8. The radiation detector of claim 1, wherein the modulator comprises a switch.

9. The radiation detector of claim 1, wherein the radiation comprises soft X-ray, ultraviolet (UV) light or extreme ultraviolet (EUV) light.

10. The radiation detector of claim 1, wherein the current source comprises a current mirror.

11. The radiation detector of claim 10, wherein the modulator is located on an input stage of the current mirror.

12. The radiation detector of claim 11, wherein the modulator comprises a current source configured to output electrical current at alternating magnitudes.

13. The radiation detector of claim 11, wherein the modulator comprises a current source configured to output two magnitudes of electrical current with adjustable ratio of durations.

14. The radiation detector of claim 10, wherein the modulator is located on an output stage of the current mirror.

15. The radiation detector of claim 1, further comprising:
a first voltage comparator configured to compare a voltage of the electrode to a first threshold;
a second voltage comparator configured to compare the voltage to a second threshold;
a counter configured to register a number of photons absorbed by the APD;
a controller;
wherein the controller is configured to start a time delay from a time at which the first voltage comparator determines that an absolute value of the voltage equals or exceeds an absolute value of the first threshold;
wherein the controller is configured to activate the second voltage comparator during the time delay;
wherein the controller is configured to cause the number registered by the counter to increase by one, if the second voltage comparator determines that an absolute value of the voltage equals or exceeds an absolute value of the second threshold.

16. The radiation detector of claim 15, wherein the controller is configured to activate the second voltage comparator at a beginning or expiration of the time delay.

17. The radiation detector of claim 15, further comprising a voltmeter, wherein the controller is configured to cause the voltmeter to measure the voltage upon expiration of the time delay.

18. The radiation detector of claim 17, wherein the controller is configured to determine a photon energy based on a value of the voltage measured upon expiration of the time delay.

19. The radiation detector of claim 15, wherein the controller is configured to connect the electrode to an electrical ground.

20. The radiation detector of claim 15, wherein a rate of change of the voltage is substantially zero at expiration of the time delay.

21. The radiation detector of claim 15, wherein a rate of change of the voltage is substantially non-zero at expiration of the time delay.

22. The radiation detector of claim 1, wherein the radiation detector comprises an array of APDs.

23. A system comprising the radiation detector of claim 1 and an X-ray source.

* * * * *